US007122579B2

(12) United States Patent
Schwartz et al.

(10) Patent No.: US 7,122,579 B2
(45) Date of Patent: Oct. 17, 2006

(54) EYE TREATMENTS USING SYNTHETIC THYROID HORMONE COMPOSITIONS

(75) Inventors: Daniel M. Schwartz, San Francisco, CA (US); John D. Baxter, San Francisco, CA (US); Michele D. Jumper, San Francisco, CA (US); Thomas S. Scanlan, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 525 days.

(21) Appl. No.: 10/374,681

(22) Filed: Feb. 25, 2003

(65) Prior Publication Data

US 2003/0175849 A1    Sep. 18, 2003

Related U.S. Application Data

(62) Division of application No. 09/371,592, filed on Aug. 10, 1999, now Pat. No. 6,555,582, which is a division of application No. 08/915,232, filed on Aug. 20, 1997, now Pat. No. 6,054,485.

(60) Provisional application No. 60/023,697, filed on Aug. 20, 1996.

(51) Int. Cl.
*A61K 31/195* (2006.01)
(52) U.S. Cl. .................................... 514/568
(58) Field of Classification Search ............... None
See application file for complete search history.

(56) References Cited

U.S. PATENT DOCUMENTS

| 2,798,053 | A | | 7/1957 | Brown | |
|---|---|---|---|---|---|
| 4,038,264 | A | * | 7/1977 | Rostoker et al. | 526/286 |
| 4,136,250 | A | | 1/1979 | Mueller et al. | |
| 4,192,827 | A | | 3/1980 | Mueller et al. | |
| 4,548,990 | A | | 10/1985 | Mueller et al. | |
| 4,870,106 | A | * | 9/1989 | Shihao | 514/567 |
| 5,474,985 | A | | 12/1995 | Polansky et al. | |
| 5,486,165 | A | | 1/1996 | Stegmann | |
| 6,221,911 | B1 | | 4/2001 | Lavin et al. | |
| 6,380,255 | B1 | | 4/2002 | Lavin | |

FOREIGN PATENT DOCUMENTS

| EP | 253717 A1 | 1/1988 |
|---|---|---|
| WO | WO 95/17178 | 6/1995 |
| WO | WO 96/40048 | 12/1996 |
| WO | WO 97/21993 | 6/1997 |

OTHER PUBLICATIONS

Alekseeva, Izv, Sibirsk. Otd. Akad. Nauk SSR, Ser. biol-Med, Nauk(2): 108-112 (1963).
Capechi, M. R. (1994) "Targeted Gene Replacement" *Scientific American*, 270(3):34-41.
Lund et al, Acta Endrocrinol. 113(1):56-58 (1986).
McDaniel et al., Journal of American Optometric Associate 67(2):109-114 (Feb. 1998).
Schiller et al., Biochim. Biophys. Acta 58-27-33 (1962).
Wall, R.J. (1996) "Transgenic Livestock: Progress and Prospects for the Future" *Theriogenology*, 45:57-68.
Wildmeister et al., Med. Welt 28(41): 1652-1655 (1977).
Yoneyama, J. (1994) "Effects of Antiglaucoma Agents on Glycosaminoglycans in Organ-Cultured Rabbit Trabecular Meshwork" *Ophthalmologica*, 208(5):278-283.
Alvarado et al., "Human trabecular cells II, Growth Pattern and Ultrastructural Characteristics", Invest, Ophthalmol. Vis. Sci., vol. 23;464-478 (1982).
Apriletti J. et al., "Large Scale Purification of the Nuclear Thyroid Hormone Receptor from Rat Liver and Sequence-specific Binding of the Receptor to DNA", J. Biol. Chem. vol. 263:9409-9417 (1988).
Apriletti J. et al., Expression of the Rat 1 Thyroid Hormone Receptor Ligand Binding Domain in Escherichia Coli and the Use of a Ligant-Induced Conformation Change as a Method for Its Purification to Homogensity, Protein Expression and Purification, vol. 6:362-370 (1995).
Ashton, P. et al., "Review, Implants", J. of Oco. Pharm., vol. 10:691-701 (1994).
Hallman V.L., "Effect of Thyroid Hormones on Intraocular Pressure," Exptl. Eye Res., vol. 6:219-226 (1967).
Jorgensen, "Thyroid Hormones and Analoge", in Hormonal Proteins and Peptides, vol. 6, Thyroid Hormones (Choh Hao Li, ed.) pp. 107-204 (1978).
Lam et al., "Hydraulie Flow Conductivity of Hyaluronic Acid Solutions: Effects on Concentration and Molecular Weight," Biorheology, vol. 27:789-795 (1990).
Lavin T.N. "Mechanisms of Thyroid Hormone Action", in Endocrinology (Degroot, Ed.), 2nd Edition, W.B. Saunders, pub. (1999).
Lewis et al., "Formation of Quinol Ethers using (Diacetoxyiodo) benzene", Synthesis, vol. 1103 (1987).
Murphy, B.P. et al., "The Determination of Thyroxine by Conpetitive Protein-binding Analysis Employing an Anion-exchange Resin and Radiothyroxine", J. Lab and Clin. Med., vol. 66:161-167 (1965).

(Continued)

*Primary Examiner*—Jean C. Witz
(74) *Attorney, Agent, or Firm*—Quine Intellectual Property Law Group, P.C.; Gary Baker

(57) ABSTRACT

The present invention involves the discovery that synthetic thyroid hormones can be used as compositions to reduce intraocular pressure in vivo. Methods of screening synthetic thyroid hormones for effect on intraocular pressure, aqueous pressure, hydraulic conductivity, hyaluronic acid secretion, and extracellular matrix assembly are provided. Methods of treating glaucoma and treating excess intraocular pressure with synthetic thyroid hormones and compositions therefore are also provided.

9 Claims, 6 Drawing Sheets

OTHER PUBLICATIONS

Oppenheimer, J.H. et al., "Stereospacific Transport of Triiodothyronine from Plasma to Cytosol and from Cytosol to Nucleus in Rat Liver, Brain, and Heart", J. Clin. Invest., vol. 75:147-154 (1985).

Polansky et al., "Trabecular Meshwork Cell Culture in Glaucoma Research, Evaluation of Biological Activity and Structural Properties of Human Trabecular Cell In Vitro", Opthalmology, vol. 91:580-595 (1984).

Polansky et al., Studies on human trabecular cells propagated in vitro, Vision Res., vol. 21:155 (1981).

Polansky et al., Human trabecular cells I: Establishment in tissue culture and growth characteristics, Invest. Opthalmol. Vis. Sci. vol. 18:1043-1049 (1979).

Ribeiro et al., "Thyroid Hormone Export Regulates Cellular Hormone Content and Response," The Journal of Biological Chemistry, vol. 271(29):17147-17151 (1996).

Samuels et al., "Depletion of L-2, 5.3'-Triiodothyronine and L-Thyroxins in Euthyroid Calf Serum for Use in Cell Culture Studies of the Action of Thyroid Hormons", J. Endocrinology, vol. 105(1):80-85 (1979).

Schwarts, H.L., et al., "Distribution and Metabolism of L-and D-Triiodothyronine (T3) in the Rat: Preferential Accumulation of L-T3 by Hepatic and Cardiac Nuclei as a Probable Explanation of the Differential Biological Potency of T3 Enantiomers", Endrocronology vol. 113:1236 (1983).

Schwarts, H.L. et al., "Quantitation of Rat Tissue Hormone Binding Receptor Isoforms by Immunoprecipitation of Nuclear Triiodothyronine Binding Capacity", J. Biol. Chem., vol. 267(17):11794-11799 (1992).

Shishiba et al., Effect of Thyroid Hormone Deficiency on Proteoglycan Synthesis by Human Skin Fibroblast Cultures, Connective Tissue Research, vol. 17:119-135 (1988).

Smith et al., "An ocular dynamic study supporting the hypothesis that hypothyroidism is a treatable cause of secondary open-angle glaucoma," Can, J. Opthtahmology, vol. 27(7):341-344 (1992).

Smith et al., "An Association between Hypothyroidism and Primary Open-Angle Glaucoma," Opthalmology, vol. 100(10):1580-1584 (1992).

Smith T.J. et al., "Regulation fo Glycosaminoglycan Synthesis by Thyroid Hormone in Vitro," J. Clin. Invest., vol. 70:1066-1073 (1982).

Smith T.J., The Effect of Thyroid Hormone on Glycosaminoglycan Accumulation in Human Skin Fibroblasts, Endocrinology, vol. 109(6):2397-2399 (1981).

Stern & Stern, "An ELIGA-Like Assay for Hyaluronidase and Hyaluronidase Inhibitors",Matrix, vol. 12(5):397-403 (1992).

\* cited by examiner

TS-5

TS-6

TS-8

TS-9

TS-10

EYE TREATMENTS USING SYNTHETIC THYROID HORMONE COMPOSITIONS

TECHNICAL FIELD

This invention relates to synthetic thyroid hormones, compositions and methods for treating elevated intraocular pressure and glaucoma.

BACKGROUND

Glaucoma afflicts approximately two million people in the United States and about 15 million people worldwide. Approximately two percent of the population over 35 suffers from some form of glaucoma and it accounts for approximately 12% of all cases of blindness. Despite its easy diagnosis, therapies to lower intraocular pressure (IOP) in patients with glaucoma are frequently inadequate. Use of topical and oral medicines to lower intraocular pressure is often limited by side effects of the drugs. In other cases, use of medical therapy to treat glaucoma is not successful in lowering intraocular pressure sufficiently to prevent progressive damage to the optic nerve.

Consequently, there is a need for methods, compounds and compositions for treating glaucoma and other medical conditions of the eye or epithelium.

SUMMARY OF THE INVENTION

Before the invention described herein, changes in IOP due to systemic changes in thyroid hormone levels, were postulated to be indirect, or if direct, such thyroid hormone-induced changes in IOP were thought to be mediated through the adrenergic $\alpha$ or $\beta$ receptors located in the eye. Aspects of the present invention now recognize for the first time an important role of thyroid hormone receptors in eye physiology. Eye thyroid receptors provide an opportunity to directly mediate thyroid hormone effects in eye cells. In particular, thyroid receptors of human trabecular meshwork ("HTM") cells can potentially mediate the amount of extracellular hyaluronic acid ("HA") maintained by HTM cells, which in turn can affect aqueous humor outflow.

The present invention recognizes that cells containing thyroid hormone receptors and cellular processes involved in GAG production would be useful components of in vitro or in vivo methods for identifying compounds that are useful as therapeutics, such as compounds that modulate glycosaminoglycans ("GAG") production. The method of identifying compounds useful for therapeutics comprises: 1) contacting a compound with cells that secrete GAG, such as trabecular meshwork cells, and 2) detecting the binding of the compound to the cells, wherein the compound has concentration of 10 micromolar or less.

In addition the present invention recognizes that thyroid hormones and synthetic thyroid hormones (STHs) can directly modulate GAG production or HA secretion from cells, such as trabecular meshwork cells. Methods of the invention, consequently, are directed to modulating GAG production or HA secretion using compounds, especially STHs, that reduce the amount or activity of such substances or cellular processes in the desired cells or tissues. Preferably, such cells will be trabecular meshwork cells, ciliary cells of the eye, endothelial cells of the eye, non-eye endothelial cells, and fibroblasts of skin and internal organs. In most instances non-systemic application of a STH is preferred, although STHs can be administered systemically as well.

The present invention also provides for a method of treating glaucoma comprising administering to an eye in need thereof an ophthalmically effective amount of a synthetic thyroid hormone to the eye. Modes of administration include topical, intraocular implantation or injection, and systemic. Preferably administration of a STH to the eye is topical administration with an eye compatible pharmaceutical carrier or non-systemic administration via a surgically implantable or injectable device, which may comprise a biodegradable or non-biodegradable polymer capable of sustained release of the STH intraocularly. Ocular inserts containing STH in a sustained release polymer may also be used.

DESCRIPTION OF SPECIFIC EMBODIMENTS

Figure 1:
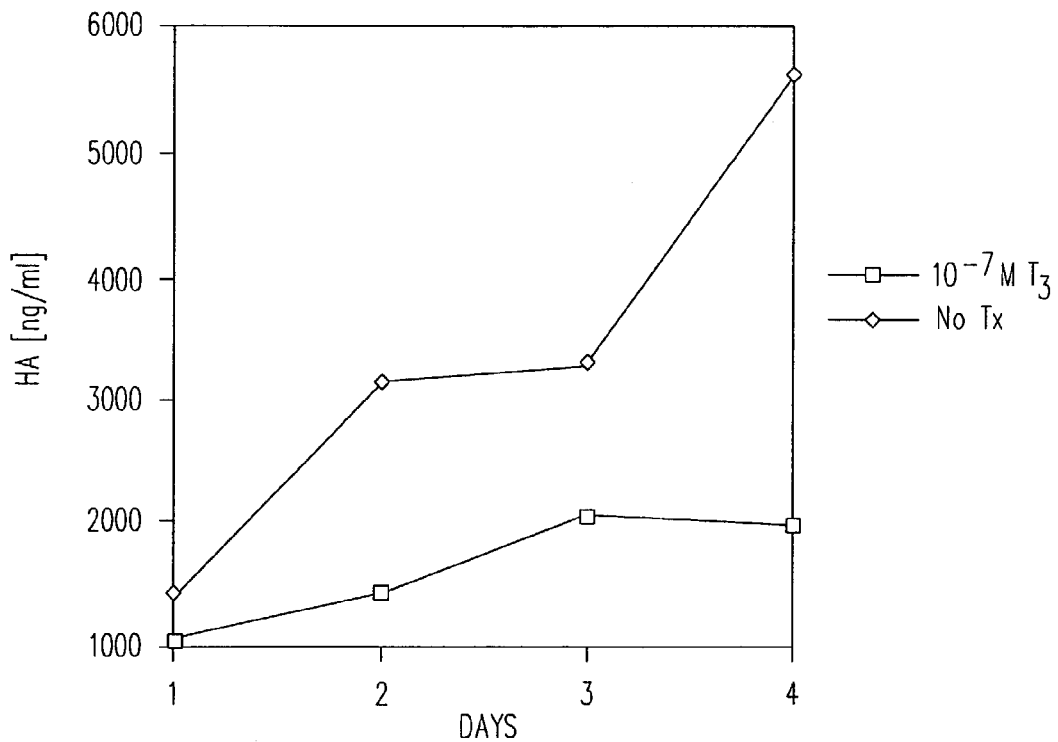
FIG. 1 shows a graph comparing HA production by HTM cells cultured in either $T_3$-supplemented or $T_3$-stripped media (No Tx). By day 2, there was a comparative 57% reduction in HA secretion from the $T_3$-supplemented cells. By day 4, this difference increased to 66%.

Abbreviations
 HA refers to hyaluronic acid.
 GAG refers to glycosaminoglycans.
 HTM refers to human trabecular meshwork.
 IOP refers to intraocular pressure.
 STH refers to synthetic thyroid hormone.

Definitions
 Intraocular pressure ("IOP") typically refers to the pressure associated with the aqueous compartments within the eye, specifically the anterior chamber. Intraocular pressure can be measured by applanation or Schiøtz tonometry as described herein. In human non-glaucomatous populations, IOP appears normally distributed. As measured by applanation tonometry, IOP mean values are 15.4 ($\sigma \pm 2.5^*$) mm Hg (sitting) and 16.5 ($\sigma \pm 2.6$) mm Hg (reclining). As measured by Schiøtz tonometry, the IOP mean value is 16.1 ($\sigma \pm 2.8$) mm Hg. Non-glaucomatous patient IOP values are only approximations. The actual frequency distribution of intraocular pressures in the population may be skewed toward the higher levels due to different subpopulations (e.g., glaucoma and age) in the general population.

Glaucoma typically refers to IOP of an individual eye that causes impairment of visual function or produces damage to the optic nerve. As a general guide an IOP over 21 mm Hg (mean+$2\sigma$) should occur in less than 2.5% of the general population, and a pressure of over 24 mm Hg (mean+$3\sigma$) in less than 0.15% of the general population. IOPs over 21 mm Hg often indicate the development of glaucoma and IOPs over 24 mm Hg are a strong indication of glaucoma. Since individual eyes vary in their susceptibility to visual impairment over time or optic nerve damage from elevated IOP, elevated IOP values must be viewed as indicative, rather than diagnostic, of glaucoma. Visual field and optic nerve assessment is also preferably evaluated to insure that an individual does not have an abnormally high IOP. Glaucoma includes both closed and open angle glaucoma. Closed angle glaucoma refers to apposition of the trabecular meshwork to the iris. Open angle glaucoma refers to resistance to aqueous outflow in or beyond the trabecular meshwork. Glaucoma also includes reference to low tension glaucoma which refers to optic nerve damage at normal IOP.

Synthetic thyroid hormone ("STH") typically refers to a molecule that binds to the thyroid receptor and acts either as an agonist, partial agonist or antagonist of normal thyroid receptor hormone function. Agonist refers to a molecule that simulates the action of normally occurring molecule when it binds to its receptor. Usually, STHs will be agonists or partial agonists of $T_3$ function and made using chemical synthesis routes. STHs usually do not include $T_3$ and $T_4$ isolated from naturally occurring tissues because purer preparations of chemically synthesized $T_3$ and $T_4$ are readily available. STHs known in the art or novel STHs useful in reducing hyaluronic acid ("HA") secretion from cells, especially in HA secretion in the eye, are further described herein. Preferably, a STH will reduce HA secretion from cultured human trabecular meshwork cells at a concentration of 10 μM or less compared to HA secretion in the absence of thyroid hormones or in media stripped of thyroid hormones. STH includes ester derivatives of STHs.

For the purposes of this invention a "thyroid hormone" or "thyroid hormone-like compound", which terms are used interchangeably herein, is any chemical entity, including peptides, which at least partially binds to thyroid hormone receptor TR-α or β with a chemical affinity constant, KD, lower than 1 μN when tested in receptor binding assay, (described in Lavin, T. N. Mechanisms of Thyroid Hormone action. In the textbook of Endocrinology (DeGroot, Ed.), 2nd Edition, W. B. Saunders, pub. (1989) and Apriletti J. et al J. Biol. Chem. 263 p. 9409–9417, 1988) using pure or substantially pure natural or recombinant thyroid hormone α or β receptor containing the ligand binding domain or thyroid hormone receptor containing preparations such as rat nuclei. Such ligands may be considered hormones when they have similar agonistic effects as the natural hormone or may be considered agonists when the compounds antagonize the effects of the natural hormones. Partial agonist/antagonists also may exist. (Suitable ligands may be agonists or antagonists).

Secretion, when used in the context of describing a cellular process, typically refers to a cellular process or processes of transporting a molecule from inside the cell to an extracellular location. In the case of glycosaminoglycan ("GAG"), secretion could involve a number of cellular processes, such as post-translational processing and delivery to the appropriate cellular site for export out of the cell. Secretion, however, refers to the net transport of the molecule and does not necessarily refer to a particular step in the process of secreting a molecule.

Synthesis, when used in the context of describing a cellular process, typically refers to a cellular process or processes involved in making a molecule, such as a GAG, for example HA. Because synthesis may involve export of the molecule out of the cell making the molecule, the term synthesis includes reference to the term secretion described herein.

Production, when used in the context of describing a cellular process, typically refers to a cellular process or processes involved in maintaining the steady state level of a molecule, such as a GAG, for example HA. Consequently, production refers to the cellular processes that are related to synthesis and secretion. Production also refers to cellular and extracellular processes responsible for maintaining steady state levels of a molecule, such degradation pathways and extracellular structural elements that anchor molecules to cells or in an extracellular matrix.

Ophthalmically effective amount typically refers to an amount of a therapeutic agent, such as a STH, sufficient to reduce IOP or prevent a rise in IOP in an eye, when such a therapeutic agent is delivered in a composition and corresponding administration technique to the eye tissue in need of such treatment. Typically, elevated IOP will be associated with ocular hypertension (elevated IOP without optic nerve damage), primary glaucoma, secondary glaucoma (e.g. systemic steroid treatment) or hypothyroidism. The STHs described herein can be used to treat elevated IOP associated with such medical conditions. Preferably, ophthalmically effective amount will reduce IOP enough so as to prevent optic nerve damage or visual impairment and such a reduction in IOP will be at least 10%, preferably at least 30% and most preferably at least 50% of the elevated IOP level. Expected normal IOP will be typically less than 22 mm Hg, such as 15 mm Hg (measured by applanation tonography, sitting position). Expected normal IOP should be sufficiently low to prevent optic nerve damage. The success of STH treatments for reducing IOP can also be measured using other formulae. For example, a patient may have an elevated IOP of 34 mm Hg and a target IOP of 17 mm Hg. To prevent optic nerve damage for this patient would require a 50% reduction in IOP to achieve this target IOP. Such percentages reduction in IOP can be simply described by the formula % reduction of IOP=100−100×(IOP after treatment)/(IOP before treatment). Measurement of IOP is described more fully herein as a method to monitor STH treatments of the eye and to vary dosage in order to tailor the ophthalmically effective amount to the responsiveness of different individuals to treatment. Recommended ophthalmically effective amounts for different indications and delivery techniques are described more filly herein.

Introduction

Until the present invention it was not recognized that thyroid hormones could directly modulate hyaluronic acid ("HA") synthesis in the eye or intraocular pressure ("IOP"). Previously, the role of thyroid hormones in eye physiology was not understood. It was not established whether thyroid hormones crossed the blood-brain barrier in sufficient amounts to exert a relevant physiological effect in the eye; whether eye cells, such as trabecular meshwork cells, possessed the requisite thyroid receptors to specifically mediate thyroid hormone signals; and whether thyroid hormones could directly modulate HA secretion or synthesis by trabecular meshwork cells or modulate IOP.

Before the invention described herein, changes in IOP due to systemic changes in thyroid hormone levels, were postulated to be indirect, or if direct, such thyroid hormone induced changes in IOP were thought to be mediated through the adrenergic α or β receptors located in the eye. Aspects of the present invention now permit recognition for the first time an important role of thyroid hormone receptors in eye physiology. Eye thyroid receptors provide an opportunity to directly mediate thyroid hormone effects in eye cells. In particular, thyroid receptors of human trabecular meshwork ("HTM") cells can potentially mediate the amount of extracellular HA maintained by HTM cells, which in turn can affect aqueous humor outflow.

Normally, maintenance of IOP requires balancing aqueous secretion by the ciliary body and aqueous egress through the trabecular meshwork. One of the most significant determinants of IOP is aqueous humor outflow. The major portion of aqueous humor out flow is directed through the trabecular meshwork and into the Canal of Schlemm, which drains via collector channels into the episcleral vasculature tube. Before fluid exits the eye and enters the Canal of Schlemm, fluid traverses the trabecular meshwork. The trabecular meshwork consists of, among other things, a meshwork of secreted glycosaminoglycans ("GAG"), such as secreted HA, and trabecular meshwork cells that line the tortuous exit region extending to the Canal of Schlemm. The HTM cells produce or secrete GAGs, such as HA. Because HA can increase the hydraulic resistance of a solution, which increases the force required to transport fluid across a defined distance, HA potentially acts as an important determinant of IOP, especially elevated IOP. Thus, one embodiment of the present invention is designed to advantageously modulate HA secretion from trabecular meshwork cells in the eye by administering an ophthalmically effective amount of a STH to human trabecular meshwork cells in order to reduce HA secretion or synthesis. Other embodiments of the invention do not necessarily inhibit HA secretion, such as methods directed to glaucoma treatments.

As a non-limiting introduction to the breadth of the invention, the invention provides at least five categories of useful methods, compounds and compositions:

1) methods directed to identifying therapeutic compounds for treating medical conditions related to thyroid hormones or GAG production or function,
2) methods directed to modulating GAG or hyaluronic acid production or function in GAG or hyaluronic acid related medical conditions, particularly when such conditions occur in the eye,
3) methods directed to the treatment of glaucoma using STHs,
4) compositions related to targeting STHs to the eye, such as ester and diester derivatives of synthetic thyroid hormones, and
5) compositions related to the methods described in 1–3 and the compounds described in 4.

For example, one embodiment of the invention provides for methods for identifying compounds useful as therapeutics, such as ophthalmic therapeutics, by:

1) screening compounds using cells that secrete GAGs or HA, such as HTM cells,
2) determining a change in GAG or HA production in the presence of the test compound compared to the absence of the test compound, and
3) selecting compounds useful for treating medical conditions related to GAG or HA production, such as glaucoma.

Another embodiment of the invention provides for methods for modulating the production of GAGs by cells, such as HTM cells, by applying an effective amount of STH to the cells. When the applied STH is an agonist or partial agonist of a thyroid hormone, production of GAG will usually be reduced. Another embodiment of the invention concerns STHs that can be targeted to the eye using ester derivatives that increase corneal penetration and are metabolized in the eye after being locally applied in order to minimize systemic affects of the applied STH. Combinations of the above methods, compounds and composition are also contemplated. Other methods, compounds and compositions are more fully described herein.

Drug Discovery: Methods for Screening for Modulators of Hyaluronic Acid Secretion or IOP The present invention recognizes that cells containing thyroid hormone receptors and cellular processes involved in GAG production would be useful components of in vitro or in vivo methods for identifying compounds that are useful as therapeutics, such as compounds that modulate GAG production. Usually such identifying methods would involve screening assay systems that permit high throughput automated screening. The method of identifying compounds useful for therapeutics comprises: 1) contacting a compound with cells that secrete GAG, such as trabecular meshwork cells, and 2) detecting the binding of the compound to the cells, wherein the compound has concentration of 10 micromolar or less. Such detecting of binding can include methods for assaying for relevant function (e.g. HA production) as described herein or developed in the art.

Although HTM cells are preferred for screening for ophthalmically active compounds, other cell types can be readily substituted for HTM cells, especially when such cells contain 1) thyroid receptors either endogenously expressed or expressed from a transferred gene and 2) proteins involved in the production of GAGs, such as HA synthetase, exogenously expressed or expressed from a transferred gene. For example, skin fibroblasts can be used for such assays and are a particularly desirable choice when screening for compounds that would inhibit the over-production of GAG in skin or as a convenient substitute for HTM cells when HTM cells are not available from specimens. Additionally, if non-HTM, GAG producing cells are used for such screening assays, it is desirable to select, or generate through recombinant techniques, cells that have the same thyroid receptor types as HTM cells, so as to mimic any possible inter-play between the α and β thyroid receptor sub-types in the production of GAG.

If human trabecular meshwork (HTM) cells are used to screen compounds such as STHs, the HTM cells can be prepared as described herein or in Polansky et al., Trabecular meshwork cell culture in glaucoma research, Ophthalmology, 1984; 91:580–595; Polansky et al., Human trabecular cells I: Establishment in tissue culture and growth characteristics, *Invest. Ophthalmol. Vis. Sci.* 1979; 18:1043–1049; Alvarado et al., Human trabecular cells II: Ultrastructural characteristics of cultured trabecular cells, *Invest. Ophthalmol. Vis. Sci.*, 23:464–478 (1982); and Polansky et al., Studies on human trabecular cells propagated in vitro, *Vision Res.*, 1981; 21:155, each of which are hereby incorporated by reference. For the screening assays described herein, third to fifth passage HTM cultures can be used from cryopreserved stocks, plated approximately 10,000 cells/$cm^2$, and grown, for example for seven to ten days to post-confluency in Dulbecco's modified Eagle's (DME) medium with 10% fetal calf serum (FCS) to obtain stable endothelial-like monolayers. The GAG, HA or protein synthesis, or transcription assays for example can be performed using these stable HTM monolayer cultures. Trabecular meshwork cells can also be isolated from an eye of a rabbit, rat, mouse, pig, cat or monkey and used for assays described herein.

The assays of STHs on HTM cell division can also be evaluated on growing cultures using DME medium with 10% FCS. STH treatments can begin the day after HTM cells are plated at 2,500 cells/$cm^2$. Effects are measured during log phase of growth (7 days) and after the control cultures reaches confluency (which varies between 3 to 6 weeks, depending on the HTM cell line and the serum in the culture medium).

The binding of a compound, such as a STH, to cells used in the screening assays, such as HTM cells, can be detected using a variety of methods. Methods that directly detect the amount of compound bound to the cell can be used, such as binding assays with compounds having isotopic, spectrophotometric or fluorometric labels. Direct detection includes measuring the specific binding of compounds to an intracellular receptor inside a human trabecular meshwork cell, such as the thyroid receptor, using whole cells, isolating nuclei or chromatin or a combination thereof. Quantitation of thyroid hormone binding or analog binding can be accomplished using methods known in the art or developed in the future, including methods described by Schwartz, H. L. et al., *J. Biol. Chem.* 17:11794–11799 (1992), herein incorporated by reference. Direct detection methods will be useful in determining the affinity of a synthetic thyroid hormone for its receptor, the ability of esterified or non-esterified derivatives to bind to thyroid receptors, and an assessment of STH uptake.

Alternatively, methods that indirectly detect the amount of compound binding can be used, such as functional assays that detect STH effects on reporter gene constructs, DNA transcription, RNA levels, protein degradation or synthesis, complex sugar degradation or synthesis and GAG synthesis or degradation. Other functional measurements described herein can be used for functional assays as well. Both in vitro and in vivo methods can be used to assay the binding of compounds.

For example, it may be desired to identify compounds, such as STHs, that modulate aqueous outflow resistance in the trabecular meshwork of the eye. In such instances it will advantageous to detect binding of the compound to trabecular meshwork cells, such as HTM (human trabecular meshwork) cells, by measuring a change in GAG production or hyaluronic acid secretion from trabecular meshwork cells in the presence and absence of the compound being tested. It will be recognized that such controls can be used in any of the assays described herein and that other controls can be readily interchanged to achieve specific detection, such as using cells without detectable levels of functional thyroid receptors or by blocking the action of an added STH. Additionally, it will be recognized that in repetitive screening assays that the control values and variations in control values become well defined. In such instances it will not be necessary to routinely conduct controls because the control values and variations from those values are established and the experimental values can be appropriately determined in the absence of a control.

Once it is determined that a compound, such as a STH, binds to a cell, such as a HTM cell, useful modulators of cellular function, such as GAG production, can be selected. Selection criteria is usually based on the extent of modulation produced by the tested compound. In the case of GAG production or HA secretion (or production), compounds will usually be selected on their ability to inhibit or reduce cellular production of GAG. Such compounds will be useful for the treatment of medical conditions caused by inappropriate GAG production or HA secretion. Such compounds will also be useful in treating diminished aqueous outflow in the eye or glaucoma. Typically, compounds that inhibit GAG production by at least 10%, preferably by at least 30% and more preferably by at least 70% compared to control GAG production will be selected as useful compounds. Such percent inhibition criteria can be applied to other measurements used in assays described herein, such as detection of HA secretion, HA binding or measurement of IOP.

More specific selection criteria can be advantageously used to identify compounds that more specifically modulate a cellular process. It will be recognized that the affinity of the compounds being tested for its receptor can often dictate the specificity of the compound. Consequently, it is desirable to select compounds that bind to receptors or modulate function with a high apparent or actual affinity. In the case of STHs, affinities close the affinity of $T_3$ (0.024 nM under physiological conditions) or $T_4$ (0.26 nM under physiological conditions) for the thyroid receptor are preferred. For STHs that produce long lasting and selective effects it is desirable to select STHs with even higher affinities for the thyroid receptor or apparent affinities deduced from a functional assay, such 0.1 nM or less under physiological conditions. To achieve such desired results, new compounds or known STHs can be synthesized and screened at predetermined concentrations. Typically, synthetic thyroid hormone will decrease GAG production or hyaluronic acid secretion at a concentration of 1.0 micromolar or less, preferably 0.1 micromolar or less and most preferably 0.01 micromolar or less. Higher concentrations, such as 10 to 75 µM, may also be used, especially when the STH has a higher ED50. The percentage inhibition criteria discussed herein can be applied to these concentration selection criteria.

Identifying useful compounds for modulating cellular processes, such as GAG production, can involve both in vitro and in vivo screening assays. Typically, compounds will be first screened using in vitro assays and then screened using in vivo assays. In vivo assays and measurements described herein can be used to further select for useful compounds, such as STHs. For example, an in vitro assay will identify an STH that inhibits 40% of HA secretion with an apparent affinity of 10 nM and the STH is further assayed by topically applying the synthetic thyroid hormone to an eye of a mammal. Alternatively, the in vivo assay can be used alone to identify compounds.

Methods for Treating Medical Conditions Related to GAG Production and Hyaluronic Acid Secretion and Glaucoma The present invention recognizes that thyroid hormones and STHs can directly modulate GAG production or HA secretion from cells, such as trabecular meshwork cells. Methods of the invention, consequently, are directed to modulating GAG production or HA secretion using compounds, especially STHs, that reduce the amount or activity of such substances or cellular processes in the desired cells or tissues. Preferably, such cells will be trabecular meshwork cells, ciliary cells of the eye, endothelial cells of the eye, non-eye endothelial cells, hair follicles and fibroblasts of skin and internal organs. In most instances non-systemic application of a STH is preferred, although STHs can be administered systemically as well.

For instance, the invention includes a method of inhibiting hyaluronic acid secretion comprising non-systemically applying an effective amount of a synthetic thyroid hormone that inhibits hyaluronic acid secretion from cells that secrete hyaluronic acid and wherein the synthetic thyroid hormone at a concentration of 10 micromolar or less inhibits at least 10% of total hyaluronic acid secretion from cultured human trabecular meshwork cells after three days culture at 37° C. compared to human trabecular meshwork cells cultured in the absence of said synthetic thyroid hormone after three days of culture at 37° C. Preferably, the STH will inhibit at least 10% of HA secretion by trabecular meshwork cells at 1 to 0.1 µM concentrations, whether the cells are in isolated eye tissue or in the human trabecular meshwork of a living eye. Typically, such HA secretion inhibition methods will not include: 1) sub-conjunctival or intraocular injection of T₃ or 2) topical application of T₃ or T₄ isolated from naturally occurring tissues. Non-systemic administration includes both topical and intraocular administration. Topical administration includes, for example, sustained release from locally applied polymers and non-surgically placed sustained release devices including ocular inserts that are inserted beneath the eyelid, local application of ointments or creams, local application of solutions such as eye compatible saline solutions and other solutions and substances that are bio- and tissue-compatible with the intended cell or tissue target, and other extraocular delivery systems, including implants, contacts, wafers or tablets. Intraocular administration includes, for example, surgically implantable or injectable intraocular sustained release devices, which can include a sustained release polymer which may be biodegradable or non-biodegradable. Non-systemically applied effective amounts and effective local concentrations of active compounds and eye compatible pharmaceutical compositions, which includes carriers) are described herein.

The present invention also includes embodiments of the invention that do not necessarily rely on inhibition of GAG production or HA secretion to produce a therapeutic effect. Such embodiments of the invention include treatments for glaucoma, methods for reducing or preventing elevated IOP, such as elevated IOP associated with mineral corticoid or steroid treatment and methods for increasing tissue fluid flow or drainage, such aqueous humor outflow in the eye. Preferably these methods rely on non-systemic administration of a therapeutically effective amount of active compound to the tissue or cells in need of treatment in a mammal, preferably a human.

For example, the present invention provides for a method of treating glaucoma comprising administering to an eye in need thereof an ophthalmically effective amount of a synthetic thyroid hormone to the eye. Local administration to the eye does not normally include: 1) sub-conjunctival or intraocular injection of T₃ or T₄, 2) topical application of T₃ or T₄ isolated from naturally occurring tissues or 3) administration of T₃ or T₄ to an eye with a cataract. Preferably administration of a STH to the eye is topical administration with an eye compatible pharmaceutical carrier or non-systemic administration using an implant that can optionally contain polymers that provide sustained release of the STH intraocularly. Such controlled release of the STH can last 6 months to a year. Such implants can be osmotic pumps biodegradable matrices or intraocular sustained release devices. Implants also include an eye contact impregnated with a synthetic thyroid hormone that allows for diffusion of the synthetic thyroid hormone from the contact. For glaucoma treatments the effective amount is usually 0.01 to 40 μg per eye per day, preferably 10 to 1,000 ng, and more preferably 10–50 ng per day. Preferably, topical application includes administering at least one drop (e.g. 30–50 μl) of a solution comprising an eye compatible pharmaceutical carrier. Other dosages and effective amounts and concentrations, depending on the delivery system, are described in full detail herein. In general it is desirable to achieve a STH concentration of 1 to 50 μM in the trabecular meshwork cells of the trabecular meshwork. Higher concentrations of 10 to 1,000 nM and 100 to 10,000 mM are preferably achieved if the apparent affinity of the STH for the thyroid receptor in the eye is on the order of 10 to 100 nM (kd) and 100 to 1,000 nM (kd), respectively.

Typically, STHs that are administered to the eye (either non-systemically or systemically) will usually be active in an in vitro or in vivo assay, such as those assays described herein. For glaucoma, treatment with a synthetic thyroid hormone at a concentration of 10 micromolar or less will usually decrease hyaluronic acid secretion from cultured trabecular meshwork cells at least 10% compared to hyaluronic acid secretion from trabecular meshwork cells cultured in the absence of the applied synthetic thyroid hormone. If so desired, the efficacy of a topically applied STH can be monitored by measuring intraocular pressure before and after topically applying the STH or during the course of treatments and the dosage adjusted to the individual's responsiveness to treatment as described herein. Serum levels of STHs can also be measured to avoid unwanted systemic effects.

In the case of glaucoma treatments it will be preferable to non-systemically administer STHs so as to avoid any systemic effects due to activation or deactivation of systemically located thyroid hormones. The invention includes tissues treated with non-systemically applied STHs. For example, the invention provides for a composition comprising a synthetic thyroid hormone inside a trabecular meshwork cell; wherein the synthetic thyroid hormone has not crossed a blood-ocular barrier. Inside the cell refers to a location in the cell not in fluid contact with the extracellular environment, such as the cell's cytosol, nucleus or other organelle. The blood-ocular barrier refers to the tissues responsible for separating the tissues of the eye from the blood. Preferably, the STH inside the corneal epithelium is an esterified derivative of a synthetic thyroid hormone. The cells include trabecular meshwork cells from explants or in a living eye, ciliary cells of the eye and endothelial cells or any of the other cells and tissues mentioned herein. Typically, the concentration of STHs inside the cells will be at least 0.04 ng per dl⁻¹. The amount (free and bound) and concentration of STH in cells can be measured using methods known in the art or developed in the future, including methods described by Oppenheimer, J. H. et al., *J. Clin. Invest.*, 75:147–154 (1985); Schwartz, H. L., et al., *Endrocrinology*, 113:1236 (1983), both of which are herein incorporated by reference. Usually concentrations of free STH inside cells will be at least 1 pM, more preferably at least 10 pM and most preferably at least 100 pM.

As the use of ophthalmic steroid therapy and oral steroids became more frequent, potential side effects arise such as elevated IOP. Concern over this side-effect has become a limitation on the long-term ophthalmic use of both potent and less active steroids, especially because a number of cases were reported in which irreversible blindness has occurred due to unrecognized increased IOP. The methods and compositions of the present invention can also be used to treat patients on steroid therapy where an inappropriate elevation of IOP has been measured or when such an elevation is expected.

Elevated IOP can also arise in other medical conditions such as following intraocular surgery, after laser treatment, or trauma. IOP can be regulated by the STH either prophylactically or post-treatment or -trauma using the methods described herein.

IOP ($P_o$ in mm Hg) varies directly with the rate of secretion of aqueous humor (F in μl/min) and inversely with the facility of aqueous outflow (C):

$$P_o = F/C + P_e$$

where $P_e$=episcleral venous pressure (mm Hg). $P_e$ is preferred to $P_v$ as a more specific abbreviation for episcleral venous pressure. Administration of a STH to the eye, especially non-systemic administration, permits the clinician to increase facility of aqueous outflow (C) and decrease elevated IOP of a mammal or patient in need thereof. Such treatments, as well as other treatments described herein, can be used prophylactically in order to prevent in increase in IOP that might be associated, for instance, with onset of glaucoma, trauma, or surgery. STHs can be applied as described herein for other treatments.

Systemic treatments of glaucoma are also contemplated. Such systemic treatments can be combined with $T_3$ and $T_4$ blood level monitoring to insure that blood $T_3$ and $T_4$ levels remain at non-toxic levels as known in the art and can be monitored using methods known in the art, such as the methods described by Murphy, B. P. et al., *J. Lab and Clin. Med.*, 66:161–167 (1965). Generally, such treatments will not be used with hypo-thyroid or thyroid-hormone-replacement therapy patients, unless such patients have an identified elevated IOP medical condition and are in need of such treatment. Preferably, such patients in need of STH treatment for elevated IOP will be hyper-thyroid. Also patients needing systemic treatment with STHs can tolerate periods of hyper-thyroid-like systemic levels of $T_3$ or $T_4$, or other STHs, in order to remove an elevated IOP. The daily amounts of thyroid hormone systemically administered will range from 0.2 µg to 2.5 µg per kg per day for $T_3$ (preferably 0.2 µg to 1 µg per kg per day) and from 0.1 µg to 10 µg per kg per day for $T_4$ (preferably 1 µg to 4 µg per kg per day). Because STHs will vary in molecular weight from $T_3$ and $T_4$ it will be appropriate to adjust the amounts of STH administered accordingly. STHs' ability to decrease IOP can also be compared to $T_3$ and $T_4$ in vitro and in vivo the to establish to proper dosing regiments. At higher STH daily amounts it will be preferable to administer tapering or one-time daily doses.

The treatments described herein can also be used to prevent elevated IOP medical conditions, such as glaucoma or ocular hypertension. Patients susceptible to elevated IOPs can be effectively treated before anticipated elevations of IOP occur. Such patients include patients undergoing intraocular surgery or laser treatment.

Synthetic Thyroid Hormones

The present invention includes two classes of novel compounds. One class of compounds comprises esters derivatives of known synthetic thyroid hormones, which includes mono- and di-ester derivatives of STHs. This first class of compounds does not include ester derivatives of STHs previously known in the art although such compounds can be used with the methods of the invention. The second class of compounds comprises novel STHs and their ester derivatives. Typically, ester derivatives are a STH with an ester group at one, two, three or more positions in the following formula:

X1—O—C(O)—Y wherein X1 is defined below and Y is group compatible with an ester and the side groups of X1, for example, Y can be an alkyl, alkenyl or aryl having 2–20 c atoms. Typically, such Y groups are less than 40 atoms in size and usually less than 30 atoms in size and preferably hydrophobic and without a charge. Di-ester derivatives are typically of the formula I:

X1—O—C(O)—B—C(O)—O—X2 wherein B is a linker (usually less than 6 carbon atoms in length) and X1 and X2 are STHs of the formula I:

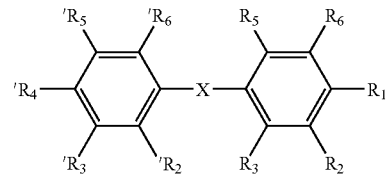

wherein $R_1$ is
—$CH_2CH(NH_2)CO_2H$, —$CH_2CH[NHCOCH\phi_2]CO_2H$, —$CH_2CH[NHCO(CH_2)_{15}CH_3]CO_2H$, —$CH_2CH[NH—FMOC]CO_2H$, —$CH_2CH[NH—tBOC]CO_2H$, —$CH_2PO_3H_2$, —$CH_2CH_2PO_3H_2$, —$CH_2CHNH_2PO_3H_2$, —$CH_2CH[NHCOCH\phi_2]PO_3H_2$, —$CH_2CH[NHCO(CH_2)_{15}CH_3]PO_3H_2$, —$CH_2CH[NH—FMOC]PO_3H_2$, —$CH_2CH[NH-tBOC]PO_3H_2$, —$CH_2SO_3H_2$, —$CH_2CH_2SO_3H_2$, —$CH_2CHNH_2SO_3H_2$, —$CH_2CH[NHCOCH\phi_2]SO_3H_2$, —$CH_2CH[NHCO(CH_2)_{15}CH_3]SO_3H_2$, —$CH_2CH[NH-FMOC]SO_3H_2$, —$CH_2CH[NH-tBOC]SO3H_2$, wherein $R_2$ is
—H, halogen, $CF_3$, OH, $NH_2$, SH, $CH_3$, -Et, wherein $R_3$ is
—H, -halogen, —$CF_3$, —OH, —$NH_2$, —$N_3$, —SH, —$CH_3$, -Et, wherein $R_5$ is
—H, -halogen, —$CF_3$, —OH, —$NH_2$, —$N_3$, —SH, —$CH_3$, -Et, wherein $R_6$ is
—H, -halogen, —$CF_3$, —OH, —$NH_2$, —SH, —$CH_3$, wherein $R'_2$ is
—H, -halogen, —$CF_3$, —OH, —$NH_2$, —$N_3$, —SH, —$CH_3$, -Et, wherein $R'_3$ is
—H, -halogen, —$CF_3$, —SH, alkyl, aryl, 5- or 6-membered heterocyclic aromatic, or cyano, wherein $R'_4$ is
H, -halogen, —$CF_3$, —OH, —$NH_2$, —SH, —$CH_3$, -Et, or an akyl, aryl or 5- or 6-membered heterocyclic aromatic attached through urea or carbamate linkages to O or N or S at the $R'_4$ position, wherein $R'_5$ is
alkyl, aryl, 5- or 6-membered heterocyclic aromatic, heteroalkyl, heteroaryl, arylalkyl, heteroaryl alkyl, polyaromatic, polyheteroaromatic, wherein said $R'_5$ may be substituted with polar or charged groups, wherein $R'_6$ is
—H, -halogen, —$CF_3$, —OH, —$NH_2$, —SH, —$CH_3$, -Et, wherein X is
O, S, $SO_2$, NH, $NR_7$, $CH_2$, $CHR_7$, $CR_7R_7$, wherein $R_7$ is alkyl, aryl or 5- or 6-membered heterocyclic aromatic, and wherein any one of the '$R_1$–'$R_6$ and $R_1$–$R_6$ groups can be replaced with a bond to B. Usually the R, to $R_7$ groups are 30 atoms or less. Preferably the di-ester derivative produces two identical molecules when hydrolyzed by hydrolysases in the cell.

Preferably, STHs are of the following structure, formula II:

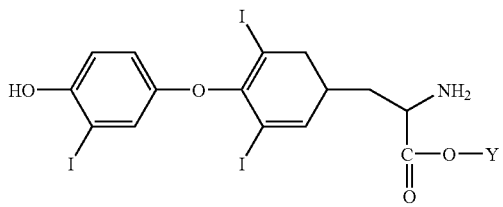

wherein Y is defined as above.  Formula II

Normally, glaucoma patients or other types of patients in need of eye treatments will administer STHs locally as eyedrops. When STHs are administered in such a manner, however, only about 0.1 to 1.0% of the dose is typically absorbed by the eye and a substantial amount of the dose can travel into the blood stream. The low absorption rate of STHs in the eye can be caused by at least three factors that can be reduced by using STH ester derivatives: 1) the drop is quickly flushed away from the surface of the eye, 2) the rapid absorption of STHs into the blood stream through the conjunctiva and/or nasal mucosa, and 3) the poor corneal penetration capability of STHs. STHs are absorbed into the eye through the cornea. In the cornea STHs are first absorbed into the epithelium layer on the eye surface containing cell membrane lipids. STHs with charged groups have reduced fat solubility, which can reduce diffusion across the corneal epithelium. If the fat solubility of the STH is improved (for example through esterification), the corneal epithelial penetration of STHs increases, resulting in greater delivery to the intraocular target tissue cells. The cornea can also act as a storage site to deliver STHs through the stroma and endothelium of the cornea into the fluid of the anterior chamber and to the trabecular meshwork cells and ciliary cells. Additionally, hydrolysis of STH ester derivatives in cells, such as trabecular meshwork cells, produces a constant diffusion gradient for the un-hydrolysed STH ester derivative into the cells. Because the concentration of un-hydrolysed STH ester derivative in the cell is kept low due to ester hydrolysis and drug formation, un-hydrolysed STH ester derivatives continually diffuse into the cell while the STH in the hydrolysed form accumulates inside the cell. Thus, ester derivatives of STHs will increase the permeability of STHs and promote accumulation of STHs in target tissues and cells.

The stability of STH ester derivatives can be tested in a buffer hydrolysis system. The ionic strength ($\mu$) of the buffers is usually 0.5. pH-values of 4.0, 6.0, 7.4 and 9.0 can be used with temperatures used including: 37° C., 50° C., 60° C. and 70° C. The half-times ($T_{1/2}$) can be calculated for the degradation constant k obtained for each studied compound ($T_{1/2}$=0.693/k; k=2.303×kk, wherein kk is the angular coefficient of the plot which illustrates the logarithm of the remaining ester as a function of time) in a buffer solution of a particular pH.

The storage stability of ester derivative of STHs under different storage conditions may be estimated by determining the degradation constants at different temperatures and calculating the degradation temperatures and calculating degradation constant k at the desired temperature from the equation of the plot corresponding to the Arrhenius equation (1), wherein log k is given as a function of [l/T].

$$\text{Log}k = \text{Log}A - \frac{E_a}{2.303R} \times \frac{1}{Y}$$

From the degradation constant (k) obtained at the desired temperature the shelf-life-time $t_{10\%}$ ($t_{10\%}$=0.104/k) which indicates the time during which 10% of the drug has degraded may be calculated.

The lipophilicity of STH ester derivative can be studied by determining partition coefficients (P) for compounds at a pH 7.40. The measurements can be made either in an octanol-aqueous buffer mixture by determining the concentration of the compound to be studied in the aqueous buffer case by HPLC. The partition coefficients of the very lipophilic compounds are, however, determined by reverse phase (RP) liquid chromatography (HPLC) from the retention time (Beckmann 116 pump and 166 UV detector; Marathon autom. sample feeder).

The half-times of enzyme hydrolysis of the novel STH ester derivatives can be determined in a plasma/buffer pH 7.4-mixture (80%–20%) at 37° C. and as known in the art.

The corneal permeability of STH ester derivatives can be evaluated by monitoring the migration of the compound from the delivering phase (epithelium side) through the cornea to the acceptor side (endothelium side) of the diffusion chamber. For example, rabbit eye cornea can be used. Samples taken from the acceptor side of the diffusion chamber, provide both the concentration of the prodrug and the liberated drug, as determined with HPLC. Thus, the rate of degradation of the prodrug in the cornea can determined, as well cornea penetration of the prodrug.

Pharmaceutical Compositions

The present invention also includes pharmaceutical compositions that can be used in the methods described herein and known in the art. Typically, the compositions will comprise a STH, particularly a STH ester derivative and a pharmaceutically acceptable carrier. Compositions are often matched with a particular mode of delivery as described herein and known in the art. The precise type and amount of STH for use in the present compositions will vary depending, for example, on the specific drug chosen, the dosage form thereof, i.e., standard versus sustained release, the condition for which the drug is administered and the size and kind of the mammal treated. Compounds of the invention, as described herein, can be selected to modulate cellular and physiological processes, for instance, to prevent an increase of IOP or to actually decrease elevated IOP. Preferably, those compounds of the present invention include STHs which provide a reduction in or a prevention of, elevated IOP when used in an amount sufficient to provide an effective concentration of $1\times10^{-7}$M or less, preferably an amount of about $1\times10^{-11}$M to about $1\times10^{-8}$M, and more preferably about $1\times10^{-11}$M to about $1\times10^{-9}$M in the aqueous or treated tissue of the eye.

For example, the invention includes a composition, preferably applied to the eye, comprising a synthetic thyroid hormone and an eye compatible pharmaceutical carrier. Preferably, such compositions include an esterified derivative of a synthetic thyroid hormone that can be optionally administered in a buffered saline solution with or without liposomes. The eye compatible pharmaceutical carrier can also comprise a biodegradable synthetic polymer. Thyroid hormones and STHs can be delivered with sustained intraocular release using biodegradable polymers. Biodegradable microsphere compositions approved for human use include the polylactides: poly(lactic acid), poly(glycolic acid), and poly(lactic-coglycolic) acid. Additional biodegradable formulations include, but are not limited to: poly (anhydride-co-imide), poly(lactic-glycolic acid), polyethyl-2-cyanoacrylate, polycaprolactone, polyhydroxybutyrate valerate, polyorthoester, and polyethyleneoxide/polybutylene teraphthalate. Intraocular implantation or injection of sustained release thyroid hormone compositions would provide long-term control (ranging from months to years) of intraocular pressure, possibly avoiding or reducing the need for topical preparations.

In another embodiment composition of the invention comprise an eye contact device (e.g. contact lens) impregnated with a synthetic thyroid hormone, preferably an esterified derivative of a synthetic thyroid hormone. For instance, dry STHs or their esterified derivatives can be supplied as tablets and dissolved in the presence of either a reusable or disposable contact in order to impregnate the contact with prodrug or drug. After suitable incubation times, such as 1 to 6 hours, the contact is rinsed of incubation solution and applied to the eye to permit the STH to diffuse into eye from the contact. It will also be advantageous to use intro-occular sustained release devices, including these described by Ashton, P. et al., *J. of Occ. Pharm.* 10:691–701 (1994).

In general, ophthalmic formulations suitable for topical and intraocular administration may be formulated and administered in accordance with techniques known to persons skilled in the art. The formulations that can oxidize are preferably prepared in an anaerobic environment by making all formulations under an inert gas. The finished formulations are preferably stored in opaque or brown containers to protect them from light exposure, and under an inert atmosphere.

Aqueous polymeric solutions, aqueous suspensions, ointments, and gels are preferably used for topical formulations. The aqueous formulations may also contain liposomes for creating a reservoir of dissolved therapeutic agent. Particularly preferred among topical formulations are gels, which enhance pre-corneal retention without the inconvenience and impairment of vision associated with ointments.

Topical ophthalmic or other topical formulations should generally include between 0.001 and 10% by weight, preferably between 0.05 and 1% by weight and most preferably 0.05 and 0.6% by weight, of the therapeutic agent in a suitable polymeric carrier. Other preferred formulations contain between 0.001 to 0.009% by weight of the therapeutic agent. As will be appreciated by those skilled in the art, the amounts of STH needed to reduce IOP or glaucoma include those amounts which will not cause appreciably systemic effects from drug or pro-drug not absorbed by the eye.

Suitable polymeric carriers include lightly crosslinked carboxy-containing polymers (such as polycarbophil), dextran, cellulose derivatives, polyethyleneglycol 400 and other polymeric demulcents.

A preferred system includes lightly crosslinked polymers of acrylic acid or the like, which are well known in the art. In a preferred embodiment, such polymers are ones prepared from at least about 90%, and preferably from about 95% to about 99.9% by weight, based on the total weight of monomers present, of one or more carboxyl-containing monoethylenically unsaturated misnomer, but other unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), embellic acid (p-hydroxycoumaric acid), and the like can be used in addition to or instead of acrylic acid.

Such polymers are cross-linked by using a small percentage, i.e., from about 0.01% to about 5%, and preferably from about 0.1% to about 2%, based on the total weight of monomers present, of a polyfunctional crosslinking agent. Included among such crosslinking agents are non-polyalenyl polyether difunctional crosslinking monomers such as divinyl glycol; 2,3-dihydroxhexa-1,5-diene; 2,5dimethyl-1,5-hexadeone; divinylbenzene; N,N-diallylacrylarnide; N,N-diallymethacrylmaide and the like. Also included are polyalkenyl polyether crosslinking agents containing two or more alkenyl ether groupings per molecule, preferably two or more alkenyl ether groupings per molecule, preferably alkenyl ether groupings containing terminal H,C=C<groups, prepared by therifying a polyhydric alcohol containing at least four carbon atoms and at least three hydroxyl groups with an alkenyl such as allyl bromide or the like, e.g., polyallyl sucrose, polyallyl pentaerythritol, or the like; see, e.g., Brown, U.S. Pat. No. 2,798,053. Diolefinic non-hydrophilic macromeric crosslinking agents having molecular weights of from about 400 to about 8,000, such as insoluble di- and polyacrylates and methacrylates of diols and polyols, diisocyanate-hydroxyalkyl acrylate or methacrylate reaction products, and reaction products of isocyanate terminated prepolymers derived from polyester diols, polyether diols or polysilaxane diols with hydroxyalkyl-methacrylates, and the like, can also be used as the crosslinking agents; see, e.g., Mueller et al., U.S. Pat. Nos. 4,192,827 and 4,136,250.

The lightly crosslinked polymers can of course be made from a carboxyl-containing monomer or monomers as the sole monoethylenically unsaturated monomer present, together with a crosslinking agent or agents. They can also be polymers in which up to about 40%, and preferably from about 0% to about 20% by weight, of the carboxyl containing monoethylenically unsaturated monomer or monomers has been replaced by one more non-carboxyl-containing monoethylenically unsaturated monomes containing only physiologically and ophthalmologically innocuous substituents, including acrylic and methacrylic acid esters such as methyl methacrylate, ethyl acrylate, butyl acrylate, 2-ethylhexylacrylate, octyl methacrylate, 2-hydroxymethyl-methacrylate, 3-hydroxypropylacrylate, and the like, vinyl acetate, N-vinylpyrrodilodone, and the like; see Mueller et al., U.S. Pat. No. 4,548,990 for a more extensive listing of such additional monoethylenically unsaturated monomers. Particularly preferred polymers are lightly crosslinked acrylic acid polymers wherein the crosslinking monomer is 2,3-dihydroxyhexa-1,5-diene or 2,3-dimethylhexa-1,5-diene.

The lightly cross-linked polymers used in practicing this invention are preferably prepared by suspension or emulsion polymerizing the monomers, using conventional free radical polymerization catalysts, to a dry particle size of not more than about 50 µm in equivalent spherical diameter, e.g., to provide dry polymer particles ranging in size from about 1 to about 30 µm, and preferably from about 3 to about 20 µm, in equivalent spherical diameter. In general, such polymers will range in molecular weight estimated to be greater than 2,000,000.

Aqueous suspensions formulated in accordance with this invention containing polymer particles prepared by suspension or emulsion polymerization whose dry particle size is appreciably larger than about 50 µm in equivalent spherical diameter are less comfortable when administered to the eye than suspensions otherwise identical in composition containing polymer particles whose equivalent spherical diameters are, on the average, below about 50 μm. Lightly crosslinked polymers of acrylic acid or the like prepared to a dry particle size appreciably larger than about 50 μm in equivalent spherical diameter and then reduced in size, e.g., by mechanically milling or grinding, to a dry particle size of not more than about 50 μm in equivalent spherical diameter do not work as well as polymers made from aqueous suspensions. One possible explanation for the difference of such mechanically milled or ground polymer particles as the sole particulate polymer present is that grinding disrupts the spatial geometry or configuration of the larger than 50 μm lightly crosslinked polymer particles, perhaps by removing uncrosslinked branches from polymer chains, by producing particles having sharp edges or protrusions, or by producing ordinarily too broad a range of particle sizes to afford satisfactory delivery system performance. A broad distribution of particle sizes will impair the viscosity-gelation relationship. In any event, such mechanically reduced particles are less easily hydratable in aqueous suspension than particles prepared to the appropriate size by suspension or emulsion polymerization, and also are less able to gel in the eye under the influence of tear fluid to a sufficient extent and are less comfortable once gelled than gels produced in the eye using the aqueous suspensions of this invention. However, up to about 40% by weight, e.g., from about 0% to over 20% by weight, based on the total weight of lightly crosslinked particles present, of such milled or ground polymer particles can be admixed with solution or emulsion polymerized polymer particle shaving dry particle diameters of not more than about 50 μm when practicing this invention. Such mixtures will also provide satisfactory viscosity levels in the ophthalmic medicament delivery systems with ease and comfort of administration and satisfactory sustained release of the medicament to the eye, particularly when such milled or ground polymer particles, in dry form, average from about 0.01 to about 30 μm, and preferably from about 1 to about 10 μm, in equivalent spherical diameter.

In another embodiment of the invention, the particles have a narrow particle size distribution. The use of a monodisperse particle will give maximum viscosity and an increased eye residence time of the ophthalmic medicament delivery systems for a given particle size. Monodisperse particles having a particle size of 30 μm and below are most preferred. Good particle packing is aided by a narrow particle size distribution.

The particles are not only subject to the upper size limits described above, but also to a narrow particle size distribution. Such use of a monodispersion of particles, which aids in good particle packing, yields a maximum increased viscosity upon contact of the suspension with the tears and increases eye residence time. At least about 80%, more preferably at least about 90% and most preferably at least about 95%, of the particles should be within a no more than about 10 μm band of major particle size distribution, and overall (i.e., considering particles both within and outside such band) there should be no more than about 20%, preferably no more than about 10% and most preferably no more than about 5% fines (i.e., particles of a size below 1 μm). It is also preferred that as the average particle size is lowered from the upper limit of 50 μm, more preferably 30 μm, to lower sizes such as 6 μm, that the band of major particle distribution be also narrowed, for example to 5 μm. Preferred sizes for particles within the band of major particle distribution are less than about 30 μm, more preferably less than about 20 μm, most preferably about 1 μm to about 5 μm.

The aqueous suspensions of this invention may preferably contain amounts of lightly crosslinked polymer particles ranging from about 0.1% to about 6.5% by weight, and preferably from about 0.5% to about 4.5% by weight, based on the total weight of the aqueous suspension. They will preferably be prepared using pure, sterile water, preferably deionized or distilled, having no physiologically or ophthalmologically harmful constituents, and will be adjusted to a neutral pH of about 7.0 to about 7.4 using any physiologically and ophthalmologically acceptable pH adjusting acids, bases or buffers, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (tr-ishydroxymethylamino-methane), or the like and salts and buffers such as citrate/dextrose, sodium bicarbonate, ammonium chloride and mixtures of the aforementioned acids and bases. The eye, however, will tolerate pH's outside the neutral range and more acidic or basic pH's can be used to facilitate drug solubility.

Aqueous suspensions can be packaged in preservative-free, single-dose non-reclosable containers. This permits a single dose of the medicament to be delivered to the eye one drop at a time, with the container then being discarded after use. Such containers eliminate the potential for preservative-related irritation and sensitization of the corneal epithelium, as has been observed to occur particularly from ophthalmic medicaments containing mercurial preservatives.

Multiple-dose containers can also be used, if desired, particularly since the relatively low viscosities of the aqueous suspensions of this invention permit constant, accurate dosages to be administered dropwise to the eye as many times each day as necessary. In those suspensions where preservatives are to be included, suitable preservatives are chlorobutanol, Polyquat, benzalkonium chloride, cetyl-bromide, and the like.

Additives which are desirably included in the topical formulations include sodium chloride, EDTA (disodium edetate), surfactants, and preservatives like BAK (benzalkonium chloride). Administration of the formulation to the eye will typically be carried out between one and four times a day, depending on the particular problem being treated.

Formulations for ocular injection fall into two classes. For subconjunctival injection, the formulations should generally include between 0.0001 and 1% by weight, preferably between 0.001 and 0.1% by weight of therapeutic agent. Any suitable carriers may be employed, preferably polymeric carriers such as dextran or polysorbate 80. Other additives which desirably may be included in the formulations are disodium edetate, sodium bisulfite and sodium sulfite. The formulation should include phosphate buffered saline, citrate buffered saline, chondroitin sulfate, or a polymeric carrier such as sodium hyaluronate (or hyaluronic acid), purified polyacrylamide or polysorbate 80. Other additives which are desirably included in the ocularly injectable formulations are sodium chloride, sodium hydroxide and hydrogen chloride, where sodium hydroxide and hydrogen chloride are used for adjustment of pH. Typically, the formulations contain between 0.001 and 1%, preferably between 0.01 and 1.0% especially when in solution, by weight of the agent.

When the active compound or prodrug is substantially in solution, it is rapidly available to exert its therapeutic function and lower concentrations may therefore be administered to achieve effective levels without causing tissue intolerance. When the active compound or prodrug is substantially in suspension, higher concentrations may be administered to achieve a sustained effective level, again without causing tissue tolerance. Hence, with solutions, lower concentrations are employed to avoid local tissue damage. With a suspension, higher concentrations are employed because a smaller dissolved amount is introduced for immediate activity.

Dosages and effective amounts to obtain desired effective concentrations for treatments for particular indications with particular individuals can be readily obtained by following the desired clinical end-point and adjusting the dosing regime appropriately. For example, in the case of STHs non-systemically administered to the eye the bioavailability of the compound is less susceptible to systemic effects. Consequently, adjustments to per day dosages and per application dosages can be varied without less potential effects from organs that interfere with drug bioavailability, such as the liver, intestine and kidney.

Clinical endpoints can be readily monitored and compared to clinical endpoints from comparable normal subjects or to clinic endpoints measured prior to treatment, as described herein and known in the art. For example, in a normal eye, variations in aqueous secretion can relate to factors such as diurnal fluctuations, aging, endocrine disturbances, hydration, drugs, and surgery result in alterations in intraocular pressure. Such variations of aqueous secretion, however, usually appear as minor compensatory adjustments in outflow facility so as to maintain a relatively constant intraocular pressure and contribute only a small effect to IOP measured over a course of treatment. As described herein, normal IOP values can be used as a reference point to indicate elevated IOP values that warrant administration of a STH or abatement or reduction of STH treatment if the eye returns to appropriate IOP levels.

In the case of glaucoma, IOP is increased and in the case of open-angle glaucoma, the outflow facilities are reduced. This results in a rise in IOP and in greater fluctuations of intraocular pressure with alterations in aqueous secretion. IOP can be measured by subjecting the eye to a force that indents or flattens it. A clinician can evaluate the course of STH treatment by measuring the change in IOP.

IOP can be measured using applanation tonometry. Preferably pressure is measured in the eye before and after treatment using a tonometer, which directly measures the force required to flatten a standard area of cornea (3.06 mm diameter). Since the applanation tonometer does not displace much fluid (approximately 0.5 µl) or increase the pressure in the eye significantly, this method is almost independent of ocular rigidity. Typically, the eye is prepared by administration of drops of 0.5% proparacaine (Ophthaine), 0.4% benoxinate (Dorsacaine), or similar topical anesthetic (but not tetracaine (Pontocaine)), the tear fluid is made fluorescent by a sterile fluorescein paper strip moistened with isotonic sodium chloride solution or distilled water. Then IOP is measured using the tonometer. The subject can be horizonal or upright. Various other tonometers and methods can also be used to measure IOP.

EXAMPLES

Example 1

Material and Methods

The following materials and methods can be used to achieve the results obtained in the examples described herein. Other methods materials and methods known in the art can also be used to achieve similar results.

Cell Culture

Primary, culture human trabecular meshwork ("HTM") cells, at a passage 3–5, were used for all experiments. Cells were cultured in DME-H16 1 g/L glucose supplemented with 15% FCS (fetal calf serum), gentamycin, glutamine (2 mm), fungizone (2.5 µg/ml), penicillin/streptomycin (UCSF Cell Culture Facility) in 11% $CO_2$ and 37° C. (standard media). The explants were incubated in a 10% $CO_2$ humidified incubator for 1–2 weeks without disturbance. By the third week in culture, cells migrated from the tissues spontaneously. At this time, the media was changed every other day and fibroblast growth factor (1 ng/ml) was added after each medium change. When the cell mass achieved a total number of 1000–2000, the explant was removed, and the cells were typsinized with STV(0.1% trypsin, 0.02% EDTA) and allowed to plate on 60 mm dishes. Media was changed every other day until the cells attained confluency, usually at day 7–8 after initial plating. Confluent cultures were either frozen at $1 \times 10^{-6}$ cells per sample in liquid nitrogen for future use, or passaged against at a split ratio of 1:32 for experimental use or continuous culture. HTM cells maintain morphology for over 20 passages. For most experiments, however, HTM cells from passage 3–5 were used. These cells are substantially pure and can be prepared by methods known in the art, such as Alvarado, et al., *Invest. Ophthalmol. Vis. Sci.*, 82:464–478 (1982). Preferably cells are grown to confluency before use in experiments, so as to diminish affects related to cell proliferation. Non-confluent cells are typically 80% confluent or less.

A $10^{-2}$ M stock 3, 3'-5-triiodo-L-thyronine ($T_3$) (Sigma, St. Louis. Mo.) was prepared in 10% DMSO/90% EtOH and stored at −20° C. Covalink-NH microwell plates (Nunc, Naperville, Ill.), N-Hydroxysulfosnccinimide (S-NHS) (Pierce, Rockford, Ill.), hyaluronic acid (ICN, Costa Mesa, Calif.), 1-Ethyl-3-(3 dimethylamino-propyl) carbodiimide (EDC) (Sigma), O-Phenylenediamine (OPD) (Calbiochem, San Diego, Calif.), Vectastain standard ABC kit (Vector, Burlingame, Calif.), were used for the hyaluronidase and HA ELISA-like assays.

Assay for Hyaluronic Acid

HTM cells were cultured in 6-well or 12-well (Corning, Corning, N.Y.) plates in 2 ml DME-H16 1 g/L glucose supplemented with 10% fetal calf serum media stripped of thyroid hormone and with or without the addition of $10^{-7}$ M $T_3$. Media was changed and collected every day or as otherwise indicated. Supernatants were concentrated and then assayed in triplicate for hyaluronic acid ("HA") by an ELISA-like assay using biotinylated hyaluronic acid binding protein HABP. Assays such as those described in Stern & Stern, *Matrix*, 12(5):397–403 (1992) can be used.

Assay for Hyaluronidase Activity

HTM cells were cultured in 100 mm dishes (Fisher, Pittsburgh, Pa.) in 10 ml serum-free DME-H 16 supplemented with insulin-transferrin-selenium with or without the addition of $10^{-7}$ M$T_3$ for number of days indicated in figure legends. Serum-free media was used to prevent the interference of hyaluronidase inhibitory proteins and hyaluronidase normally found in serum. Supernatants were concentrated in centricon (Amicon,) and assayed in triplicate for hyaluronidase activity in pH 3.7 citrate-phosphate buffer by a modification of an ELISA-like assay (Stern & Stern, *Matrix*, 12(5): 397–403 (1992) the methods of which are herein incorporated by reference) using directly biotinylated HA. All samples were assayed in triplicate.

Example 2

Figure 2:
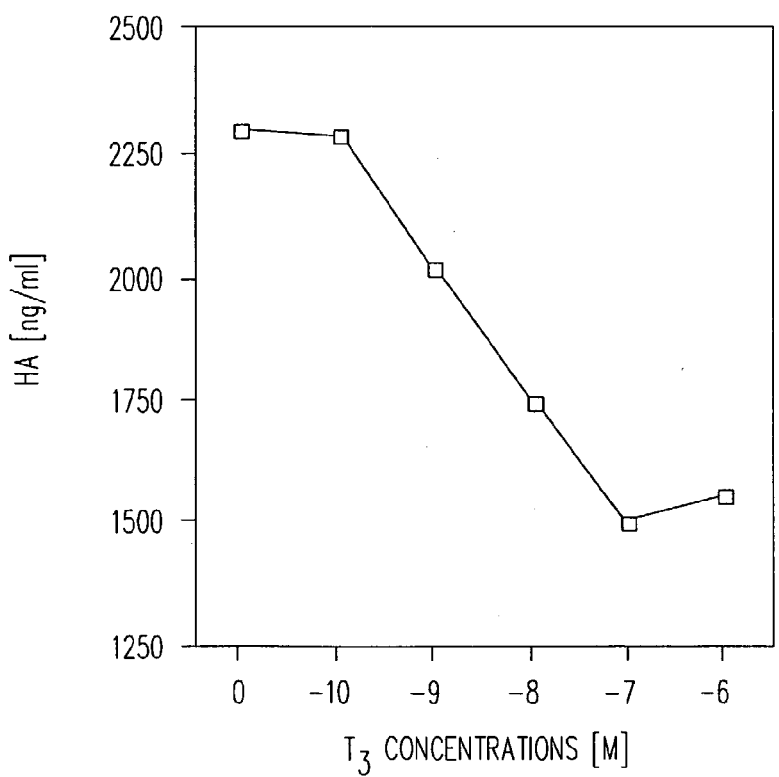
FIG. 2 shows the effect of $T_3$ concentration on HA production by cultured HTM cells. Maximal inhibition of HA production occurred between $10^{-2}$–$10^{-6}$ M $T_3$.

Synthetic Thyroid Hormone, Such as $T_3$, Inhibits HA Secretion from HTM Cells To investigate whether HA secretion could be modulated by a synthetic thyroid hormone, HTM ("HTM") cells were cultured in the presence and absence of $T_3$. HTM cells cultured in $T_3$ supplemented media showed a progressive decrease in net hyaluronic acid secretion compared to cells grown in media stripped of $T_3$, see FIG. 1. "Stripped" media refers to media in which $T_3$ has been removed using the method of anion exchange resin as described by Samuel et al. (Samuel H. H., Stanley, Cananova J: Endocrinology, July 1979, 105(1):80–5). Typically, the concentration of $T_3$ in stripped media is less than 0.1 pM. A difference in secreted HA concentration in the $T_3$ supplemented media and control media cultures (confluent cells) could be observed on day 3 of exposure to supplemented $T_3$ (final media concentration $10^{-7}$ M) as shown in FIG. 1. By day 5, there was a 2.95 fold reduction in secreted HA concentration in the supernatants from $T_3$ supplemented cultures, compared to supernatants from control cultures. The difference in HA levels continued through day ten of culture (the last day of the experiment). $T_3$ treated non-confluent (less than 75% confluent) cells also produced an even greater reduction of HA concentration in the media compared to confluent $T_3$ treated cells (each well contained approximately 250,000 cells). The half maximal concentration for reduction of HA concentration by $T_3$ was approximately 5 nM, see the dose response curve in FIG. 2 for confluent cells.

Example 3

$T_3$ Increases Secreted Hyaluronidase Activity

To investigate whether the amount of secreted of HA can be modulated, at least in part, by an increased breakdown of secreted HA in the presence of $T_3$, secreted hyaluronidase enzyme activity by HTM cells was measured in the presence and absence of $T_3$. HTM cells were cultured in serum-free media for hyaluronidase activity experiments to eliminate the complications of hyaluronidase and/or hyaluronidase inhibitory proteins found in sera. Secreted hyaluronidase activity increased in the supernatants from $T_3$ supplemented non-confluent cultures compared to controls lacking $T_3$ additions. By day 10, there was a comparative 1.9 fold increase in secreted hyaluronidase activity in the $T_3$ supplemented cultures, despite the downregulation of HA production in serum free conditions.

Example 4

CD44 Isoforms, Which Can Regulate Secreted HA Levels, Exist on HTM Cells

To investigate whether CD44 receptors are expressed by HTM cells, four CD44 isoforms can be measured using RT-PCR analysis with probes for CD44s, CD44E, CD44-v1 and CD44-v3. All isoforms are splice variants arising from in 9 external axons having alternative splicing sites. All four isoforms are expressed in HTM cells. For RT-PCR experiments, cells (1–3×106) were harvested by scraping, pelleted, immediately frozen in liquid nitrogen and stored until RNA and cDNA were made. RNA was made using RNA Track™ (Biotecx, Friendswood, Tex.). The RNA was used as a template for the first strand synthesis of cDNA in a reaction mixture containing 1000 U Moloney Murine Leukemia Virus Reverse Transcriptase (BRL, Gaithersburg, Md.), 50 mM random hexamer primer, 50 mM Tris-HCl (pH 8.3), 75 mM KCl, 10 mM dithiothreitol, 3 mM MgC12, 0.5 mM each of dGTP, dATP, dTTP and dCTP in 60 ul total volume. The cDNA reactions were carried out at 37° C. for 90 min, and then diluted 1:3 or 1:7 in water, pretreated with DEPC. Oligonucleotide primers were diluted to 40 μM in water.

For RT-PCR, a modified hot start method was used. A quantity of 3–5 μl of CDNA was added to 30 μl of a master mix containing 0.8 μmol of each primer, 17 mM Tris-HCI (pH 8.3) and 80 mM KCI. Water was added to the cDNA reactions to a final volume of 40 μl. All reactions were overlaid with light mineral oil and heated to 99° C. After 10 min the reactions were cooled to 94° C. and a 10 μl volume containing 7 mM $MgCl_2$, 1 mM each of dATP, dTTP, dGTP and dCTP, and 1.2 U Taq Polymerase (Perkin-Elmer Cetus, Branchburg, N.J.) was added directly through the oil overlay. Cycle parameters were: 95° C. for 60 sec, 55 to 57° C. for 30 sec, 72° C. for 30 sec, with a final extension of 15 min at 75° C. Reactions were cycled for 32–34 times using an automatic programmed thermocycler (Perkin-Elmer Cetus, Norwalk, Conn.). RT-PCR products were separated on 2% Low EEO agarose (Fisher Scientific, Pittsburgh, Pa.). The ethidium bromide [EtBr] gels were run at 200 V for 45 min, visualized by ultraviolet light and photographed.

Oligonucleotides for RT-PCR were made to exons within the CD44 gene in a manner that would allow for efficient amplification of all of the CD44 isoforms. Oligonucleotides were designated as forward [F] or reverse [R] and by the exon number to which they were made:

| | |
|---|---|
| F5 | 5'-GATGATGACGTGAGCGGCTC-3,; |
| F12 | 5'-CAGTCATAGTACAACGCTTCA-3,; |
| R7 | 5'-GATAAAATCTTCATGATCATC-3,; |
| R 15 | 5'ATTCAGATCCATGAGTGGTAT-3'; |
| β-actin forward | 5'-GCTCTCTTCCAGCCTTCC-3'; |
| β-actin reverse | 5'-AGAGCCACCAACCCACACAGAG-3'. |

Such CD44 isoforms can bind HA and regulate, at least in part, receptor mediated endocytosis of secreted HA. In this pathway, HA is internalized via CD44 receptors and directed to lyzosomes for breakdown by hyaluronidase. Furthermore, CD44s and CD44E have been shown to anchor HA and other GAGs to the cell surface without endocytosis.

Example 5

$T_3$ Decreases the Expression of CD44 Isoforms

To determine whether $T_3$ affects secreted HA turnover by the HTM through alternative splicing of the CD44 receptor gene, CD44 expression can be monitored using RT-PCR, as described herein. When HTM cells are were exposed to supplemental $T_3$ for 18 hours there is a dramatic reduction in the expression of the CD44E and CD44-v 3 isoforms. Thus, a $T_3$ induced decrease in CD44 expression is consistent with decreased binding of HA and other GAGs to trabecular cells.

Example 6

Human Eyes Contain Aqueous $T_4$

To investigate whether a human aqueous humor contains $T_4$, $T_4$ is measured using a direct dialysis technique (Corning Nichols Institute, San Juan Capistrano, Calif.) from aqueous obtained during cataract surgery on patients without known thyroid disease. A pooled sample of aqueous specimens showed a free $T_4$ level of 0.4 ng/dL. No $T_3$ could be measured in the same specimens.

Example 7

Human TM Cells of the Eye Have Thyroid Hormone Receptors

To investigate whether a human eye contains thyroid hormone receptors, particularly HTM cells, thyroid hormone receptors are measured using antibodies to the thyroid hormone receptor with immuno-histochemistry or RT-PCR analysis for thyroid receptor nucleic acids using HTM cells. Thyroid hormone receptors α 1, 2 and β 1 were found using both assays and non-specific binding was comparatively low.

Example 8

Topical Administration of $T_3$ to and Eye In Vivo, Results in $T_3$ Diffusion into the Cornea and into the Anterior Chamber To investigate the ability of synthetic thyroid hormones to penetrate the tissues of the eye, $I^{125}$-$T_3$ was administered to rabbit eyes in vivo and radioactivity measured in the aqueous humor. Briefly, the following procedure can be used to measure penetration of a thyroid hormone into an eye: 1) anesthetize rabbit with 2:1 Ketamine:Xylazine, 2) apply 1 drop of topical anesthetic to the eye, 3) rinse the eye with Balanced Saline Solution (Alcon) and dab dry, 4) apply 30 ul of $I^{125}$-$T_3$ in 100% EtOH solution or 30 ul or $I^{125}$ $T_3$ in 30% DMSO in PBS (phosphate buffered saline), 5) allow the $T_3$ solution absorb for 30 min to 1 hour for an alcohol solution and 45 min for DMSO solution, 6) allow the $T_3$ solution to absorb for about 30 seconds in the control eye, 7) rinse the eye with 60 ml of sterile water prior to withdrawal of 50 ul of aqueous humor with a disposable syringe, and 8) measure the radioactivity from the aqueous humor sample in a gamma counter. Autoradiography was performed on rabbit eyes that were enucleated 2 hours after administration of topical $I^{125}$-$T_3$. Label was concentrated over the aqueous outflow channels of the eye indicating that topically administered $T_3$ can bind to the trabecular meshwork. Using such a method approximately 0.125% of the applied $T_3$ diffuses into the aqueous humor after 45 to 60 minutes and the diffusion is independent of whether alcohol or DMSO is used as a solvent for $T_3$. Thus, $T_3$ is able to diffuse across the diffusion barrier of the cornea and is therefore accessible to the aqueous and trabecular meshwork.

Example 9

Topical Administration of $T_3$ to an Eye In Vivo, Lowers Intraocular Pressure To investigate the effects of a synthetic thyroid hormone, such as $T_3$, on intraocular pressure ("IOP"), $T_3$ was topically administered to rabbit eyes in vivo. Normal pigmented Dutch rabbits were used for the IOP experiments and $T_3$ was topically administered to the right eye of a rabbit as 30 µl of a 1 mM $T_3$ sterile solution of PBS with 30% DMSO vehicle four times per day. 30% DMSO vehicle was applied four times per day to the control left eye. At the indicated times IOP was measured using the technique of pneumotonometry.

In clinical situations lower amounts of $T_3$ would normally be administered to reduce potential systemic toxicity or disturbances, such as tachycardia effects.

| RABBIT | IOP WEEK 1 OD/OS | IOP WEEK 2 OD/OS | IOP WEEK 3 OD/OS | % REDUCTION IOP WEEK 3 OD/OS |
|---|---|---|---|---|
| 1 | 25.5/26.0 | 23.0/23.0 | 19.0/21.5 | 25/17 |
| 2 | 25.0/23.5 | 23.5/22.5 | 21.5/21.5 | 14/9 |
| 3 | 21.5/22.0 | 22.5/22.0 | 21.0/19.5 | 2/11 |
| 4 | 26.0/26.5 | DIED | | |
| 5 | 25.5/25.0 | 23.5/20.0 | 23.5/22.0 | 8/12 |
| 6 | 24.0/24.0 | 20.5/21.5 | 23.0/22.5 | 4/16 |

Five rabbits showed at least some detectable decrease in IOP within three weeks of administration and one rabbit showed as much as a 25% decrease in IOP after three weeks of $T_3$ administration. The observed reduction in IOP in both eyes may be related to systemic absorption of the topically administered $T_3$. Measured serums levels of $T_3$ were elevated in these rabbits after 2 weeks of topical treatment (range of 176–427 ng/dL with normal range of 88–160 ng.dL). One rabbit died, possibly due to $T_3$ toxicity from the high serum $T_3$ concentrations resulting form topical administration. $T_3$ toxicity can be avoided by reducing the amount of synthetic thyroid hormone applied, using less active STHs or using low concentrations of pro-drug ester derivatives of STHs as described herein.

Example 10

Hydraulic Conductivity of Cultured Human Trabecular Meshwork Cells: An IN VITRO Model of Aqueous Outflow As a measure of thyroid hormone's ability to effect HTM function in vivo we assessed whether $T_3$ can act directly to increase fluid flow across a monolayer of HTM cells in vitro. We used an in vitro model for measuring hydraulic conductivity. The model measures the hydraulic conductivity of confluent monolayers of HTM cells.

Monolayers of HTM cells were grown on Millipore filters in polystyrene holders. The holders were mounted in a device that measures the pressure difference that develops as a fluid flows across a known resistance. Two pressure gauges, one upstream of the known resistor and one downstream of the known resistor but just upstream of the filter holder with the HTM cells measure the pressure difference. Since the outer surface of the filter is at atmospheric pressure, the pressure at the second gauge is the perfusion pressure of the cells. Hydraulic conductivity is equal to Q/PA, where Q is the flow, P is the perfusion pressure, and A is the surface area of the monolayer.

Confluent HTM cells were grown for 4 or 8 days on 1 cm Millipore filters (Millipore Corp., Bedford, Mass.) in DMEM-H16 containing, 2 mM glutamine, 1 nM penicillin, and 1 nM streptomycin. The medium also consisted of 10% fetal bovine serum that had been stripped of hormones by incubation with activated charcoal and a mixed cation/anion exchange resin (AG 501-X8 Resin, Bio-Rad, Hercules, Calif.). Confluent HTM cells were grown for 4 or 8 days either with or without $10^{-7}$M $T_3$. The control cells were treated with the appropriate amount of the ethanol vehicle. Hydraulic conductivity of each filter will be measured over 30 min while perfusing the cells with the same medium they were grown in and expressed as µl/min/mm Hg/cm². All of the experiments were done in quadruplicate.

Figure 3:
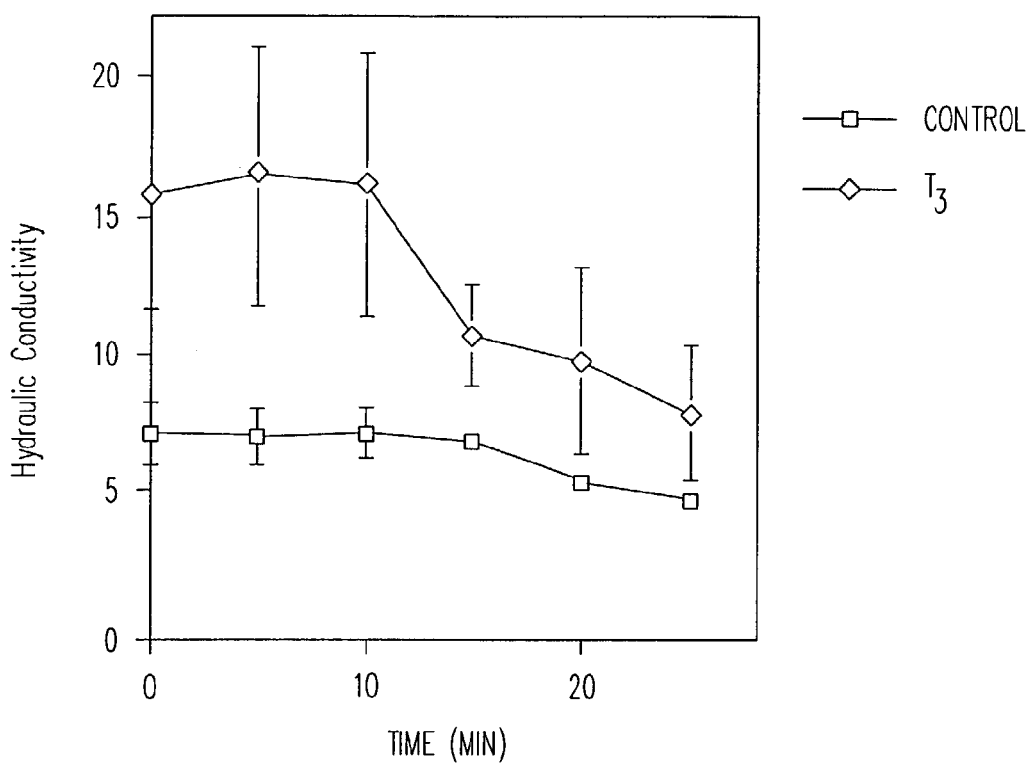
FIG. 3 is a chart showing hydraulic conductivity of HTM cells incubated for 4 days with 10-7 M T3 or without T3. The control cells, which were not treated with T3, were treated with an appropriate amount of an ethanol vehicle.
Figure 4:
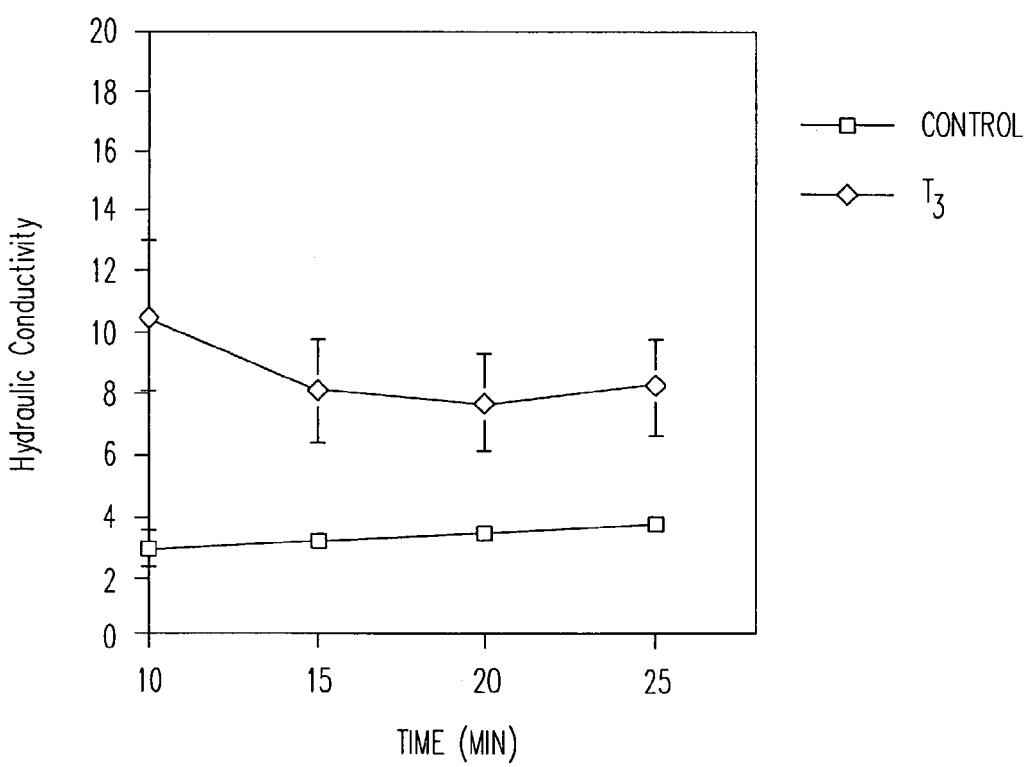
FIG. 4 is a chart showing hydraulic conductivity of HTM cells incubated for 8 days with 10-7 M T3 or without T3.

After 4 days of treatment, HTM cells incubated with $T_3$ had a 1.5 to 2-fold greater hydraulic conductivity than HTM cells grown in the absence of $T_3$ (FIG. 3). However, this difference was not statistically significant (Wilcoxon test). After 8 days of treatment, HTM cells incubated with $T_3$ had a statistically significant 2 to 3-fold greater hydraulic conductivity than HTM cells grown in the absence of $T_3$ ($p=0.0286$, Wilcoxon test) (FIG. 4). Thus, $T_3$ acts directly on confluent layers of HTM cells to decrease their resistance to fluid flow and increase their hydraulic conductivity. Further, the magnitude of this effect is similar to previously reported studies with epinephrine, a anti-glaucomatous agent that increases aqueous outflow and reduces intraocular pressure. The results are significant because in vitro measurements of hydraulic conductivity correlate well with observed effects of ocular drugs such as epinephrine and corticosteroids on aqueous outflow in vivo. Therefore, since $T_3$ increases hydraulic conductivity in vitro, it may increase aqueous outflow in patients with glaucoma and reduce intraocular pressure.

Example 11

$T_3$ Regulates Attachment of Extracellular Matrix to Cultured Human Trabecular Meshwork Cells We have demonstrated that HTM cells grown in the presence of $T_3$ produce less hyaluronic acid than HTM cells grown in the absence of $T_3$. Hyaluronic acid (HA) normally interacts with cells by binding to a cell surface receptor, CD44, to form an extracellular matrix. In order to assess whether $T_3$ administration effects the ability of HTM cells to bind to HA and assemble an extracellular matrix, we assayed the ability of HTM cells grown in culture to bind to HA and assemble it into a visible extracellular matrix. The assay system visualizes the cell's extracellular matrix by taking advantage of its ability to exclude added formalinized red blood cells from an area around the cell. Proteoglycan monomer and HA are added to the cells in excess as pericellular matrix assembly is observed by microscopy. Since matrix assembly around trabecular meshwork cells is an important constituent of resistance to aqueous outflow, regulation of this matrix may be one determinant of intraocular pressure.

HTM cells were plated on 35-mm dishes at a density of $1 \times 10^4$ cells per plate. Cells were grown for 2 or 6 days either with or without $10^{-7}$M $T_3$ in DMEM-H16 containing, 2 mM glutamine, 1 nM penicillin, and 1 nM streptomycin. The medium also consisted of 10% fetal bovine serum that had been stripped of hormones by incubation with activated charcoal and a mixed cation/anion exchange resin (AG 501-X8 Resin, Bio-Rad, Hercules, Calif.). For exogenous matrix assembly, cells were then incubated for 3 hours at 37° C. with 3.0 mg/ml of aggregating proteoglycan monomer (purified from rat chondrosarcoma tumor (Ref. 1)) and 15 μg/ml of hyaluronan (grade 1, Sigma Chemical Co., St. Louis, Mo.). The medium was removed and 0.75 ml of a suspension of formaldehyde fixed red blood cells ($1 \times 10^8$ cells/ml) in phosphate buffered saline with 0.1% bovine serum albumin was added to each well of cells. After 10 minutes the cells and extracellular matrices (ECMs) were observed visualized by phase contrast microscopy (REF 2, 3). The cell matrices were categorized into one of three groups. Cells having no coats have no visible ECM. Cells having small coats have a visible ECM that extends less than the width of the cell's nucleus out from the cell's plasma membrane. Cells having large coats have a visible ECM that extends greater than the width of the cell's nucleus out from the cell's plasma membrane.

Cells grown for 2 days in the presence of $10^{-7}$M $T_3$ had about a 2-fold greater number of cells with no coats than did cells grown in the absence of $T_3$. After 4 days of treatment with $10^{-7}$M $T_3$ this difference increased to more than 4-fold. Thus HTM cells treated with $10^{-7}$M $T_3$ bind less HA and assemble smaller ECMs than do cells grown in $T_3$ free medium. $T_3$ may thus act to either displace ECM from trabecular cells, or alternatively, may inhibit ECM assembly synthesis. In either case, reduction of the cellular bound ECM may reduce aqueous outflow resistance and reduce intraocular pressure.

Example 12

Synthesis of STHs

Many TR (thyroid receptor) ligands are known in the art, including T4 (thyroxine), T3, T2 and TS-9. See Jorgensen, Thyroid Hormones and Analogs, in 6 *Hormonal Proteins and Peptides, Thyroid Hormones* 107–204 (Choh Hao Li ed., 1978), incorporated by reference herein.

The syntheses of several TR ligands are described below.

Synthesis of TS1, TS2, TS3, TS4, TS5

TS1, TS2, TS3, TS4 and TS5 and analogs thereof can all be prepared by simple acylation of the nitrogen atom of any thyronine analog, including T3 (3,5,3'-triiodo-L-thyronine), T4 (thyroxine) and 3,5-diiodothyronine. TS1 and TS2 are synthesized by reacting T3 with $Ph_2CHCO_2NHS$ (N-hydroxy succinimide-2,2-diphenylacetate) and $C_{16}H_{33}CO_2NHS$, respectively. TS3 is synthesized by reacting T3 with FMOC-Cl (fluorenylmethyloxycarbonyl-chloride). TS4 is synthesized by reacting T3 with $tBOC_2O$ (tBOC anhydride or di-t-butyldicarbonate). TS5, which differs from TS1–4 by having a —H instead of an —I at the $R^1_3$ position, is synthesized by reacting 3,5-diiodothyronine with $tBOC_2O$. The general reaction scheme for TS1, TS2, TS3, TS4 and TS5 is depicted in FIG. 3. It should be noted that in the reaction scheme, both TS5 and its precursor both have a hydrogen rather than an iodine at the $R^1_3$ position.

Synthesis of TS6 and TS7

TS6 is synthesized by reacting TS5 with paranitrophenylisocyanate. TS7 is synthesized by reacting TS6 with TFA (trifluoroacetic acid), which cleaves the tBOC group. These reactions are simple organic synthesis reactions that can be performed by anyone of ordinary skill in the art. The synthetic scheme for TS6 and TS7 is diagrammed in FIG. 4.

Synthesis of TS8

Figure 5:
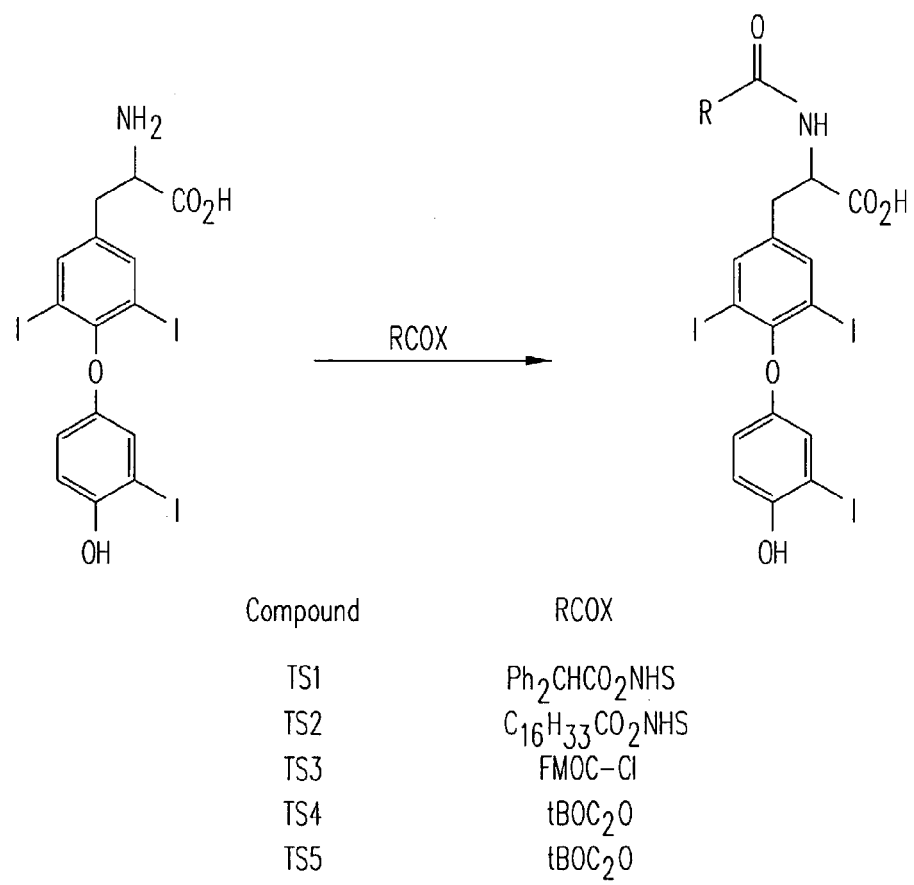
FIGS. 5–9 show the structures of various STHs.
Figure 7:
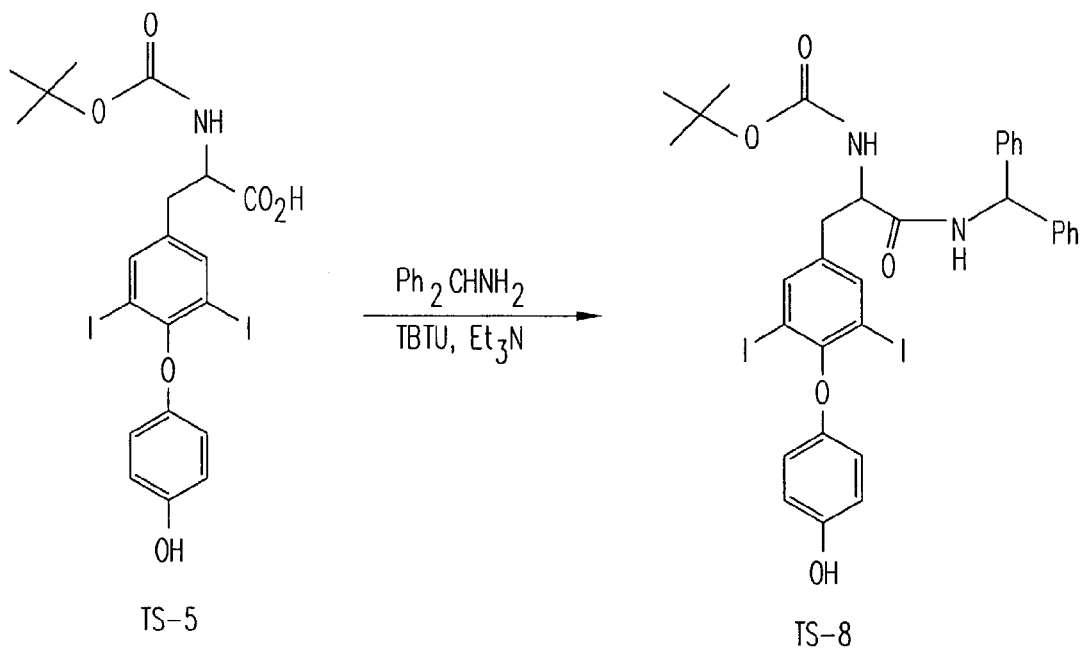

TS8 is synthesized by reacting TS5 with $Ph_2CHNH_2$ (diphenylmethylamine) in the presence of triethylamine and any amide forming condensing reagent, such as TBTU (hydroxybenztriazoleuronium tetrafluoroborate) or HBTU (hydroxybenztriazoleuronium hexafluorophosphate). The synthesis scheme for TS8 is depicted in FIG. 5.

Synthesis of 3,5-diiodio-3'Isopropylthyronine Derivatives

For designing a class of antagonists, it is important to have a hydrophobic group at the 3' position as well as an extension at the 5' position. Preferred hydrophobic groups at the 3' position include: methyl, benzyl, phenyl, iodo, and heterocyclic structures. The synthesis of a 3,5-diiodo-3'-isopropyl-5'-substituted thyronine is described below. The example provided describes the specific steps for synthesizing the TS10 compound, but this general reaction scheme can be used by one of ordinary skill in the art to synthesize any number of 3,5,-diiodo-3'-isopropyl-5'-substituted thyronine derivatives, which are characterized by having an extension at the 5' position. Additional compounds of this class can be synthesized using known organic synthesis techniques.

Figure 6:
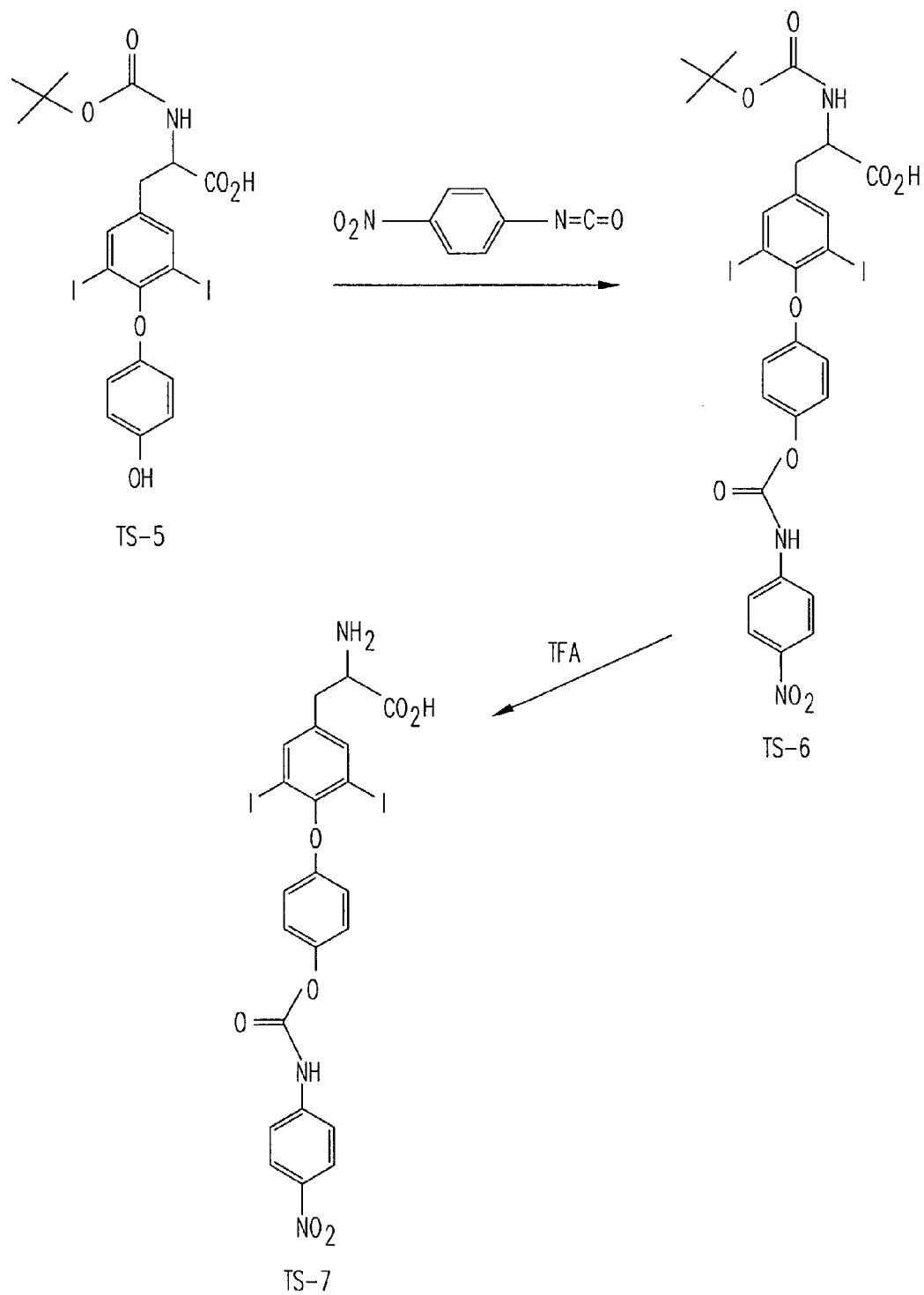
Figure 8:
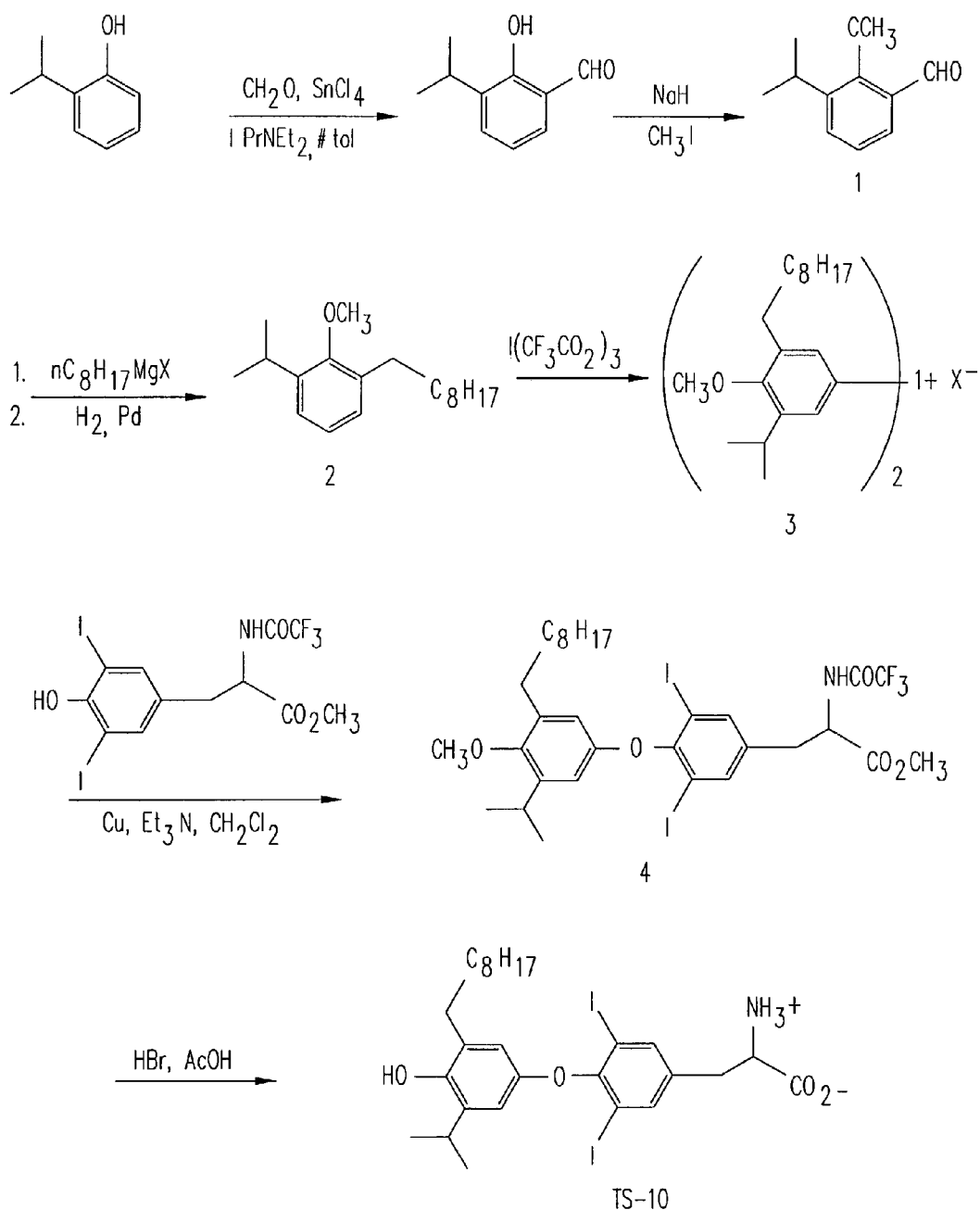
Figure 9:
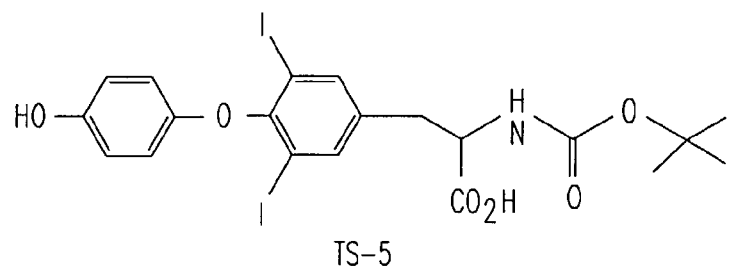
Figure 9:
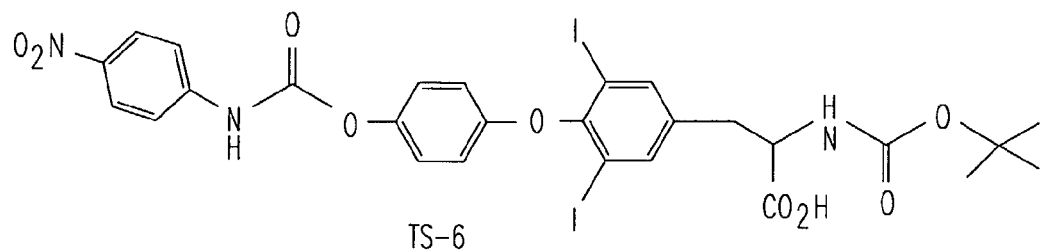
Figure 9:
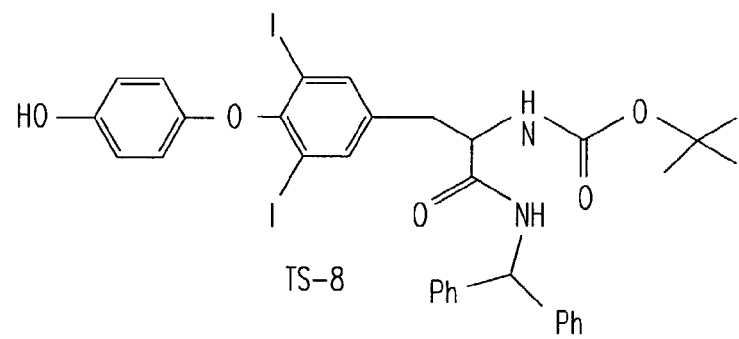
Figure 9:
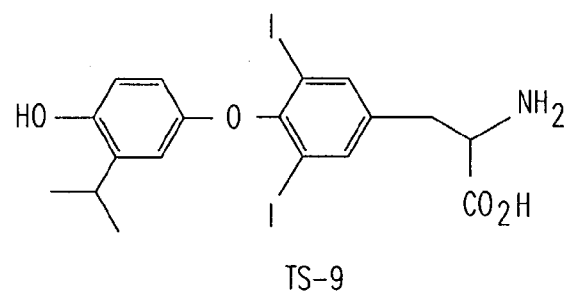
Figure 9:
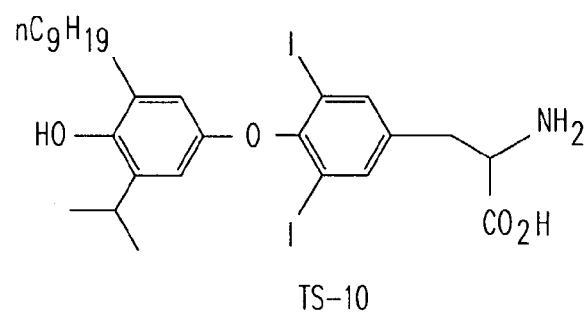

The synthesis of TS10 is described below and is depicted in FIG. 6. Numbers used in the reaction scheme for TS10 indicating the reaction product for each step are in parentheses.

2-Formyl-6-isopropylanisole (1): 2-formyl-6-isopropylanisole (10.0 g, 61 mmol), as made by Casiraghi, et al. JCS Perkin I, 1862 (1980) (incorporated by reference), is added dropwise to a suspension of sodium hydride (3.7 g, 153 mmol) in 50 mL THF and 50 mL of DMF in a round bottom flask. The addition generates an exothermic reaction and formation of a gray solid. Methyl iodide (26.0 g, 183 mmol) is then added dropwise and the reaction mixture is stirred at room temperature for 5 hours. The reaction mixture is quenched with 20 mL of water, then poured into 500 mL of water, and is extracted with ether (2×300 mL). The ether layers are combined, washed with water (5×1000 mL), dried over magnesium sulfate and concentrated in vacuo to provide 10.2 g (94%) of the title compound, with the following $^1$H NMR (CDCl$_3$) properties: d 10.30 (s, 1H), 7.63 (d, 1H, J=3 Hz), 7.50 (d, 1H, J=3 Hz), 7.13 (t, 1H, J=3 Hz), 3.81 (s, 3H), 3.31 (heptet, 1H, J=7.5 Hz), 1.19 (d, 6H, J=7.5 Hz).

2-(2-Hydroxynonyl)-6-isopropylanisole (not shown in scheme): Octylmagnesium chloride (8.4 mL, 16.9 mmol, 2.0 M) is added dropwise to a solution of 1 (1.5 g, 8.4 mmol) in 10 mL THF at −78° C. The reaction mixture is stirred for 2 hours with warming to room temperature. The reaction mixture is diluted with 50 mL ether and poured into 50 mL water. The ether layer is washed with brine (1×50 mL), dried over sodium sulfate, and concentrated in vacuo. Flash chromatography (silica gel, 10% ether/hexane→15% ether/hexane) provides 734 mg (30%) of the title compound with the following $^1$H NMR (CDCl$_3$) properties: d 7.33–7.10 (m, 3H), 5.00 (br. s, 1H), 3.81 (s, 3H), 3.33 (heptet, 1H, J=7 Hz) 1.90–1.19 (m, 14H), 0.86 (t, 3H, J=6.5 Hz); HRMS (EI), found: 292.2404; calc'd: 292.2402.

2-nonyl-6-isopropylanisole (2): Compound 2 (663 mg, 2.3 mmol) is dissolved in solution of 5 mL ethanol and 5 mL acetic acid, and a spatula tip of palladium on carbon catalyst is added. The reaction mixture is then charged with hydrogen gas (using a simple balloon and needle) and the mixture is stirred at room temperature overnight. The next day, the reaction mixture is poured into ether (100 mL) and the ether layer is extracted with saturated sodium bicarbonate (3×100 mL). The ether layer is dried over sodium sulfate and concentrated in vacuo to provide 581 mg (91%) of (2) with the following $^1$H NMR (CDCl$_3$) properties: d 7.14–7.00 (m, 3H), 3.75 (s, 3H), 3.36 (heptet, 1H, J=6.8 Hz), 2.63 (t, 2H, J=7.5 Hz), 1.68–1.15 (m, 14H), 0.86 (t, 3H, J=5.5 Hz); HRMS (EI), mass found: 276.2459; calculated: 276.2453.

Thyronine adduct (4): Fuming nitric acid (0.071 mL) is added to 0.184 mL acetic anhydride chilled to −5° C. Iodine (66 mg) is added to this mixture followed by trifluoroacetic acid (0.124 mL). This mixture is stirred for 1 hour with warming to room temperature, at which point all of the iodine is dissolved. The reaction mixture was then concentrated in vacuo to provide an oily semi-solid material. The residue was dissolved in 0.7 mL of acetic anhydride and cooled to −20° C. A solution of anisole (2) (581 mg, 2.1 mmol) in 1.2 mL acetic anhydride and 0.58 mL TFA is added dropwise. The reaction mixture is stirred at −20° for 1 hour, then stirred overnight with warming to room temperature. The reaction mixture is partitioned between water and methylene chloride. The methylene chloride layer is dried over sodium sulfate and concentrated in vacuo to provide the iodonium salt (3) as an oil. This material is not purified or characterized, and is directly introduced into the coupling reaction.

N-Trifluoroacetyl-3,5-diiodotyrosine methyl ester (552 mg, 1.0 mmol) prepared according to the procedure of N. Lewis and P. Wallbank, *Synthesis* 1103 (1987) (incorporated by reference) and all of the crude iodonium salt (3) from above is dissolved in 5 mL of anhydrous methanol. Diazabicyclo[5.4.0]undecane (DBU) (183 mg, 1.2 mmol) and a spatula tip of copper-bronze are added and the resulting mixture is stirred at room temperature overnight. The next day, the reaction mixture is filtered, and the filtrate is concentrated in vacuo. The crude residue is purified by flash chromatography (silica gel, 10% ethyl acetate/hexane) to provide 30 mg (4%) of the protected thyronine adduct (4).

Deprotected thyronine (TS10): The protected thyronine 4 (30 mg, 0.04 mmol) is dissolved in a mixture of 2.25 mL acetic acid and 2.25 mL 49% hydrobromic acid. The reaction mixture is heated to reflux for 5 hours. The reaction mixture is cooled to room temperature, and the solvents are removed in vacuo. Water is added to triturate the oily residue into a gray solid. This solid material is filtered, washed with water, and dried over P$_2$O$_5$ in vacuo to provide 24 mg (81%) of the title compound, TS10, with the following $^1$H NMR (CDCl$_3$) properties: d 7.57 (s, 1H), 6.86 (s, 1H), 6.45 (s, 1H), 6.34 (s, 1H), 4.81 (m, 1H), 3.86 (s, 3H), 3.71 (s, 3H), 3.33–3.05 (m, 3H), 2.58–2.47 (m, 2H), 1.62–0.76 (m, 23H); MS (LSIMS): M$^+$=817.0.

As mentioned above, this reaction scheme can be modified by one of ordinary skill in the art to synthesize a class of compounds characterized by 3,5-diiodo-3'isopropylthyronine derivatives, wherein (1) the 3' isopropyl group can be replaced with a hydrophobic group, including methyl, benzyl, phenyl, iodo, and heterocyclic structures, and (2) a wide variety of chemical structures can be incorporated at the 5' position, including alkyl groups, planar aryl, heterocyclic groups, or polar and/or charged groups.

The aldehyde (1) in the above reaction scheme is a versatile synthetic intermediate which allows for the attachment of a variety of chemical moieties to the 5' position of the final thyronine derivative. In addition, a variety of chemical reactions can be used to attach the chemical moieties. These reactions are well known in the art and include organometallic additions to the aldehyde (including Grignard reagents, organolithiums, etc.), reductive amination reactions of the aldehyde with a primary or secondary amine, and Wittig olefination reactions with a phosphorous ylid or stabilized phosphonate anion. Other possibilities include reduction of the aldehyde to a benzyl alcohol allowing for etherification reactions at the 5' position. As mentioned above, these methods allow for a wide variety of chemical structures to be incorporated at the 5' position of the final thyronine derivative, including alkyl groups, planar aryl, heterocyclic groups or polar and/or charged groups.

TABLE 1 and FIG. 6 depict the structures of several TR ligands.

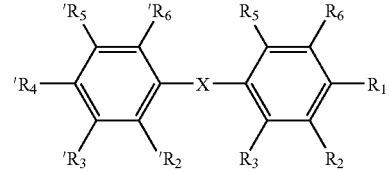

FORMULA 1

TABLE 1

| Cmpd | $R_3$ | $R_4$ | $R_5$ | $R^1_3$ | $R^1_4$ | $R^1_5$ | $R_1$ |
|---|---|---|---|---|---|---|---|
| $T_3$ | —I | —O— | —I | —I | —OH | —H | —$CH_2CH(NH_2)CO_2H$ |
| $T_4$ | —I | —O— | —I | —I | —OH | —I | —$CH_2CH(NH_2)CO_2H$ |
| TS1 | —I | —O— | —I | —I | —OH | —H | —$CH_2CH[NHCOCHø_2]CO_2H$ |
| TS2 | —I | —O— | —I | —I | —OH | —H | —$CH_2CH[NHCO(CH_2)_{15}CH_3]CO_2H$ |
| TS3 | —I | —O— | —I | —I | —OH | —H | —$CH_2CH[NH-FMOC]CO_2H$ |
| TS4 | —I | —O— | —I | —I | —OH | —H | —$CH_2CH[NH-tBOC]CO_2H$ |
| TS5 | —I | —O— | —I | —H | —OH | —H | —$CH_2CH[NH-tBOC]CO_2H$ |
| TS6 | —I | —O— | —I | —H | —OC(O)NH = $Ø_pNO_2$ | —H | —$CH_2CH[NH-tBOC]CO_2H$ |
| TS7 | —I | —O— | —I | —I | —OC(O)NH = $NHØNO_2$ | —H | —$CH_2CH(NH_2)CO_2H$ |
| TS8 | —I | —O— | —I | —H | —NH—CHØØ | —H | —$CH_2CH[NH-tBOC]CO_2H$ |
| TS9 | —I | —O— | —I | —IsoPr | —OH | —H | —$CH_2CH(NH_2)CO_2H$ |
| TS10 | —I | —O— | —I | —IsoPr | —OH | —$(CH)_8$—$CH_3$ | —$CH_2CH(NH_2)CO_2H$ |

\* Prior Art Compound
-Ø: phenyl
-ØpNO$_2$: para nitro phenyl wherein $R_6$, $R_2$ and $'R_3$ represent H in Formula 1 and X is O.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition comprising a synthetic thyroid hormone inside a trabecular meshwork cell; wherein said synthetic thyroid hormone has not crossed a blood-ocular barrier.

2. The composition of claim 1, wherein said synthetic thyroid hormone is a esterified derivative of a synthetic thyroid hormone.

3. The composition of claim 1, wherein said trabecular meshwork cell is an human trabecular meshwork cell from an eye explant.

4. The composition of claim 1, wherein said synthetic thyroid hormone is bound to a human thyroid receptor.

5. The composition of claim 4, wherein said synthetic thyroid hormone has a concentration inside said trabecular meshwork cell of at least 0.04 ng per $dl^{-1}$, and wherein said trabecular meshwork cell is a human trabecular meshwork cell.

6. A composition comprising a synthetic thyroid hormone and an eye compatible pharmaceutical carrier; wherein said synthetic thyroid hormone is an esterified derivative of an synthetic thyroid hormone or wherein said eye compatible pharmaceutical carrier comprises liposomes.

7. The composition of claim 6, wherein said eye compatible pharmaceutical carrier comprises a buffered saline solution.

8. The composition of claim 6, wherein said eye compatible pharmaceutical carrier comprises a biodegradable synthetic polymer.

9. A composition comprising an eye contact impregnated with a synthetic thyroid hormone wherein said synthetic thyroid hormone is an esterified derivative of a synthetic thyroid hormone.

\* \* \* \* \*